(12) United States Patent
Chen et al.

(10) Patent No.: US 8,290,227 B2
(45) Date of Patent: Oct. 16, 2012

(54) METHOD AND SYSTEM FOR DIAGNOSTICS SUPPORT

(75) Inventors: Shoupu Chen, Rochester, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 768 days.

(21) Appl. No.: 12/412,438

(22) Filed: Mar. 27, 2009

(65) Prior Publication Data

US 2010/0246884 A1    Sep. 30, 2010

(51) Int. Cl.
G06K 9/00  (2006.01)
(52) U.S. Cl. ...................................... 382/128
(58) Field of Classification Search .................. 382/128
See application file for complete search history.

(56) References Cited

U.S. PATENT DOCUMENTS

| | | | |
|---|---|---|---|
| 6,243,095 B1 * | 6/2001 | Shile et al. | 715/854 |
| 8,019,138 B2 * | 9/2011 | Reicher et al. | 382/128 |
| 2002/0159622 A1 | 10/2002 | Schneider et al. | |
| 2003/0190067 A1 * | 10/2003 | Tsujii | 382/132 |
| 2004/0062429 A1 * | 4/2004 | Kaufhold | 382/132 |
| 2005/0069184 A1 * | 3/2005 | Kasai | 382/128 |
| 2005/0267337 A1 * | 12/2005 | Sakai et al. | 600/300 |
| 2006/0222225 A1 * | 10/2006 | Kurahashi | 382/128 |

OTHER PUBLICATIONS

Franco Pestilli et al. "How do attention and adaptation affect contrast sensitivity?", *Journal of Vision*, 7(7):9, p. 1-12.

* cited by examiner

*Primary Examiner* — John Strege

(57) ABSTRACT

A method for displaying a diagnostic image acquires the diagnostic digital image and applies one or more pattern recognition algorithms to the acquired diagnostic digital image, detecting at least one feature within the acquired diagnostic digital image. At least a portion of the acquired diagnostic digital image displays with a marking at the location of the at least one detected feature. At least one detected feature displays under a first set of image display settings for a first interval, then under at least a second set of image display settings for a second interval.

19 Claims, 24 Drawing Sheets

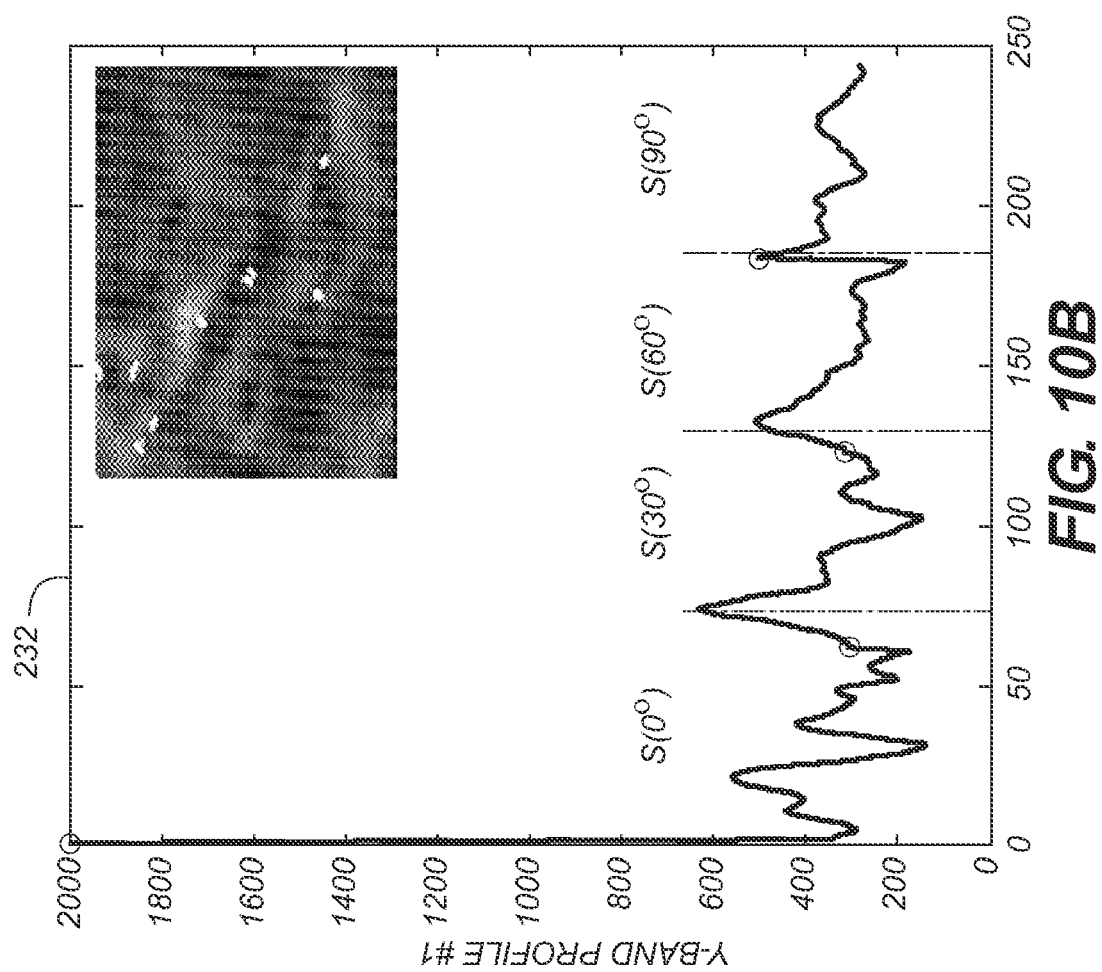

METHOD AND SYSTEM FOR DIAGNOSTICS SUPPORT

FIELD OF THE INVENTION

The invention relates generally to medical imaging systems and more particularly to a medical decision support system that applies cognitive function principles to methods for medical diagnostic display.

BACKGROUND OF THE INVENTION

Pattern recognition is a branch of artificial intelligence concerned with the systematic classification or description of observations. Pattern recognition aims to classify visual data (in particular, patterns) based either on a priori knowledge or on statistical information extracted from the patterns. The patterns to be classified are generally groups of measurements or observations, defining points in an appropriate multidimensional space.

Techniques in Computer-Aided Detection (CAD) mammography, a promising tool in diagnostic breast imaging, apply pattern recognition algorithms to digital mammographic images. Using various pattern recognition utilities, the mammography CAD system helps the radiologist to identify abnormalities that might otherwise have been overlooked in the breast image.

A sizeable percentage of the abnormalities (particularly true-positive or TP indications) detected in the mammogram are microcalcifications (MCCs). Microcalcifications are tiny deposits of calcium that can indicate likely breast cancer sites, particularly when they appear to be grouped as microcalcification clusters. An MCC cluster itself comprises a plurality of MCC spots, each of which, in turn, comprises a plurality of mammographic image pixels.

When a mammography CAD system uses pattern recognition algorithms to detect lesions in mammographic images, some error is inevitable. As a result, normal structures that resemble lesion patterns may be inaccurately classified as abnormalities. These mis-classified normal structures are called false positives (FPs).

An efficient CAD algorithm yields a high true-positives (TPs) rate while keeping the number of false-positives (FPs) to a minimum. In studying the performance of existing CAD utilities using digital or film-based mammograms, it has been found that many FP MCC candidates identified by mammography CAD systems lie on or near normal features that are generally linear such as blood vessels. Removing those MCC candidates that are associated with linear structures but do not represent likely true-positives can significantly reduce the overall FP rate. However, in practice, there seem to be unlimited variations in the appearance of linear structures in terms of contrast, brightness, texture and morphological shapes, and other characteristics.

Various methods for extracting linear structures have been proposed, with significant differences between the different approaches. One promising approach has been implemented as a multi-scale line operator, for example, with intuitively convincing results. The output of such a method can then be used for classifying linear structures.

The overall function of such a line operator can be described as follows: The line operator takes the average grey level of the pixels lying on an oriented local line passing through the target pixel, and subtracts the average intensity of all the pixels in the locally oriented neighborhood. The line strength is compared for n orientations. Line direction is obtained from the orientation that provides maximum line strength. Scale information can be obtained by applying the line operator to images that are rescaled by Gaussian smoothing and sub-sampling. For each pixel, the scale that produces the maximum line strength is taken as the detected line scale.

Another method estimates the intensity profile of curvilinear structures (CLS) in mammograms in a single scale. In this type of method, the CLS are assumed to have circular cross section when the breast is not compressed. The cross section of CLS in the mammogram is assumed to be elliptical. Candidate pixels for CLS are detected using the response of a second order difference operation which is applied in four directions. If there is a sufficient high response for one of the orientations, the pixel forms part of a CLS. A measure of line strength is obtained by determining the contrast of the line profile at these pixels. Other researchers have adopted this two step method and devised a multi-resolution ridge detector for structures ranging from 1800 microns to 180 microns, for example. Additional improvements to this method enhance the performance of the detector by using local energy thresholding to suppress undesirable response from noise. The local energy is also used to determine CLS junctions.

Alexander Schneider et al. (U.S. Patent Application Publication No. US 2002/0159622 proposes a system and method for detecting lines in medical images. The method describes a direction image array and a line image array are formed by filtering a digital image with a single-peaked filter, convolving the regular array with second-order difference operators oriented along the horizontal, vertical, and diagonal axes, and computing the direction image arrays and line image arrays as direct scalar functions of the results of the second order difference operations. Schneider et al. noted that, if the four line operator function correspond to the special orientations of 0, 45, 90 and 135 degrees, line detection based on the use of four line operator functions requires fewer computations than line detection based on the use of three line operator functions.

FP reduction, although addressed using a number of different approaches, remains a problem. One type of approach for FP identification uses features extracted from spatial and morphology domains, including gray-level description, shape description and clusters description. However, researchers have not directed their attention to the use of features directly related to linear structures for this purpose.

It has been held by some researchers that the results from a multi-resolution ridge detector could be beneficial to false-positive MCC reduction, but there has been no conclusive evidence of such a reduction. Moreover, it can be computationally inefficient to generate actual linear structures merely for the purpose of confirming the association of an MCC candidate cluster with a linear structure in mammography CAD. (Note that an MCC candidate cluster is a cluster that is under testing for cancerous lesions.)

Thus, although researchers have explored the relationship of MCC clusters to nearby linear features in various ways and have attempted to classify various groupings of MCC spots in order to detect likely cancer sites, results achieved thus far indicate that there is still considerable room for improvement. It is desirable to be able to identify TPs wherever possible in the mammography image. At the same time, any increase in the relative number of FPs can make a mammography system difficult to use effectively as a diagnostic tool.

No matter how well CAD algorithms can be made to perform, it is observed that CAD processing is primarily a tool for assisting the diagnostician and, as such, has its limitations. Ultimately, diagnosis itself relies on the judgment of the medical practitioner, who may be guided and heavily influenced by mammography CAD results. One problem in assessing CAD output relates to inherent difficulties in visual perception when the mammographic image is displayed, particularly where MCC clusters may be detectable using a proven algorithm but are difficult to discern clearly and appear against a relatively "noisy" background. Existing systems are not adaptable or configurable to compensate for such conditions, but, instead, force the viewer to overcome difficulties in visually identifying and classifying potential MCC features. This difficulty, in turn, can tend to reduce the value of improved CAD techniques, since their results may not provide clear diagnostic information to the viewing practitioner when the image is displayed.

Therefore, not only is an improved approach for microcalcification detection in mammography CAD of value; it is also desirable that the image content display apparatus and display methods be used more effectively to aid the diagnostician in utilizing mammography CAD detection results for making diagnostic decisions.

SUMMARY OF THE INVENTION

An object of the present invention to advance the art of computer-assisted diagnosis, particularly with respect to mammography imaging. With this object in mind, embodiments of the present invention provide a method for displaying a diagnostic image, comprising: acquiring the diagnostic digital image; applying one or more pattern recognition algorithms to the acquired diagnostic digital image and detecting at least one feature within the acquired diagnostic digital image; displaying at least a portion of the acquired diagnostic digital image with a marking at the location of the at least one detected feature; and displaying the at least one detected feature under a first set of image display settings for a first interval, then under at least a second set of image display settings for a second interval.

It is a feature of the present invention that it adapts and employs cognitive function principles to the task of displaying detected features in a diagnostic image.

Advantageously, embodiments of the present invention help to make detected features within a radiograph or other diagnostic image more readily visible to a viewing diagnostician.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 10B is another graph illustrating an exemplary curve of ensemble average of sets of lines in a rotatable band when the band is at different angles.

DETAILED DESCRIPTION OF THE INVENTION

Figure 1:
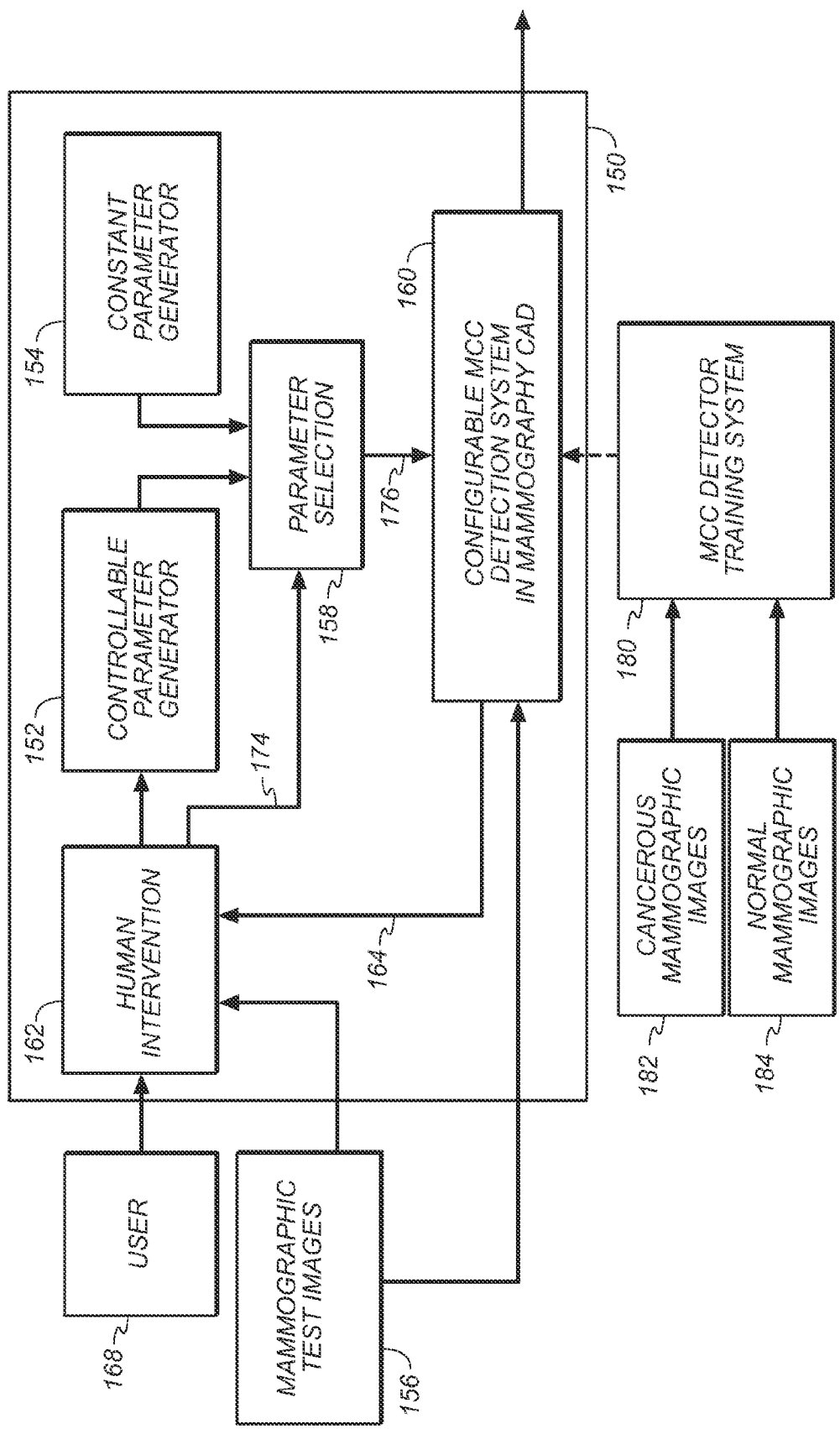
FIG. 1 is an illustration of an embodiment of the method for microcalcification detection for the current invention.

The following is a detailed description of embodiments of the invention, reference being made to the drawings in which the same reference numerals identify the same elements of structure in each of the several figures.

In embodiments of the method of the present invention for medical decision support, the diagnostic images can include digitized X-ray film images, as well as images acquired by a range of possible digital imaging devices (such as computed radiography or CR, digital radiography or DR, computed tomography or CT, magneto-resonance imaging or MRI devices, for example.). Pattern recognition algorithms, as the term is used herein, can include conventional classification algorithms for diagnostic imaging and known in the art, and also the exemplary microcalcification detection algorithms that are depicted in FIG. 1 in the present invention.

In microcalcification diagnosis, cancerous mammographic images contain mass and microcalcification lesions that are confirmed as true positives (TPs) by radiologists. Normal mammographic images, on the other hand, do not contain mass or microcalcification (MCC) lesions.

A mammographic test image is an image under test for cancerous lesions. The mammographic test image may or may not contain either or both mass or microcalcification lesions. An MCC detector is optimized to detect microcalcification lesions, including those in mammographic test images.

As was noted earlier in the background section of this disclosure, there can be almost unlimited variation in how linear structures appear, in terms of contrast, brightness, texture and morphological shapes, and other characteristics, for example. This high degree of variability introduces a significant measure of complexity to the diagnostic problem. Some parts of this task rely most heavily on the skill set of the human observer, with respect to creativity, use of heuristics, flexibility, and common sense. Other parts of this task can benefit from judicious use of computerized logic processing, including speed and accuracy of computation, focus, and dedication to an assigned task. Embodiments of the present invention address the diagnostic problem by combining the strengths of both human perception and computational processing, achieving a synergistic integration of these two approaches.

Synergy of human and computer capabilities can be realized by incorporating a detection parameter control into the detection process. Embodiments of the present invention provide an integrated solution to the MCC detection problem by constructing a configurable detection system. FIG. 1 is a block diagram of a detection system 150 illustrating an embodiment of a workflow for microcalcification detection according to the present invention. In FIG. 1, there is provided a parameter selection step 158 that allows a human operator, viewer 168, to participate in the process loop. Parameter selection step 158 selects a set of parameters either from a constant parameter generator 154 or from a controllable parameter generator 152 or, alternately, from the viewer. Parameter selection step 158 sends the selected parameters to a detection process 160 through a path 176. Controllable parameter generator 152 is manipulated by viewer 168 through a human intervention step 162. Viewer 168 receives input information from test images 156 or feedback 164 from the detection output and makes a decision to use parameters either from the constant parameter generator 154 or from the controllable parameter generator 152, or to use other suitable user-entered values. This configurable system can then be configured or reconfigured by commands from the human operator, viewer 168, through a command line 174.

Figure 2A:
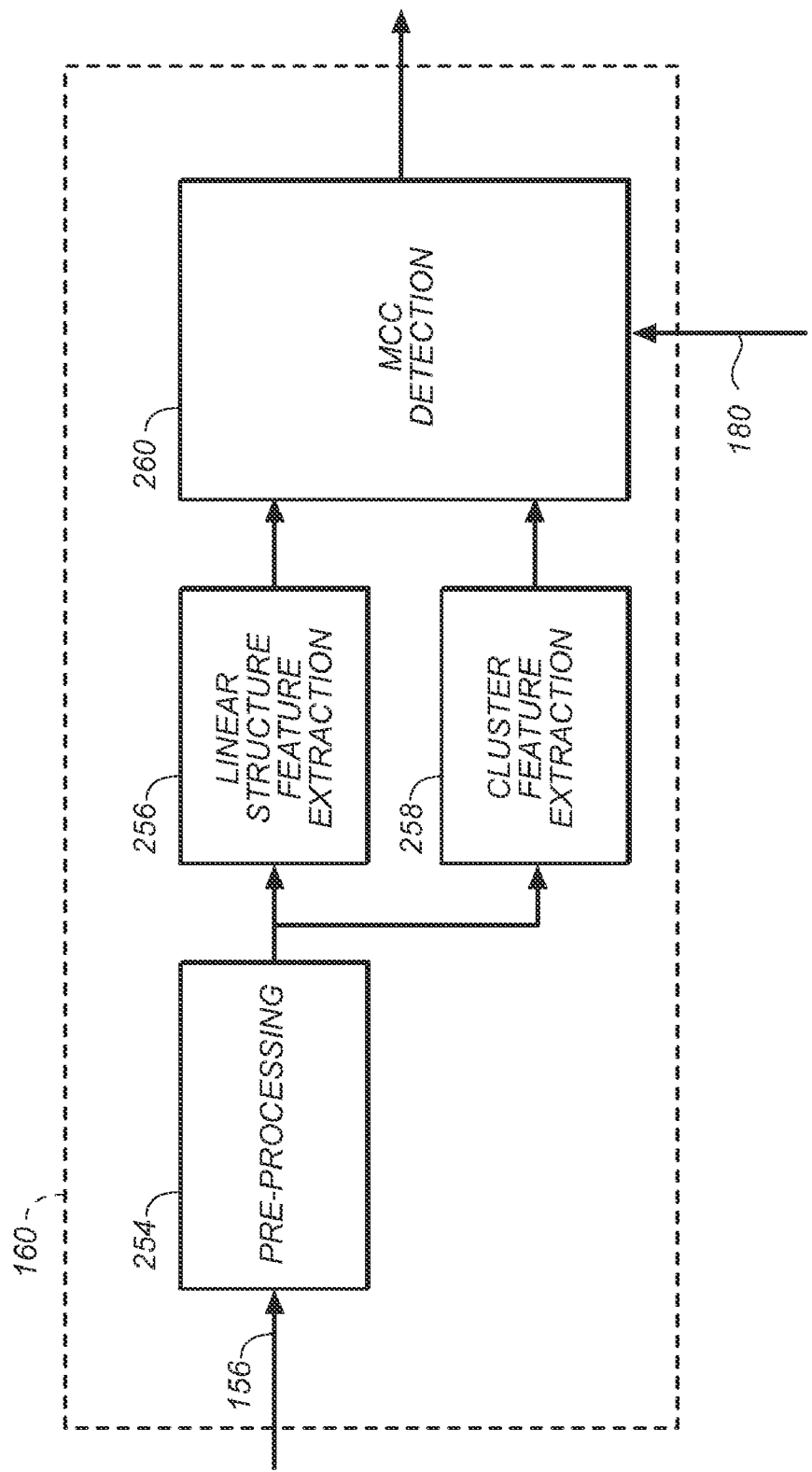
FIGS. 2A and 2B show exemplary workflows for MCC detection for embodiments of the current invention.
Figure 2B:
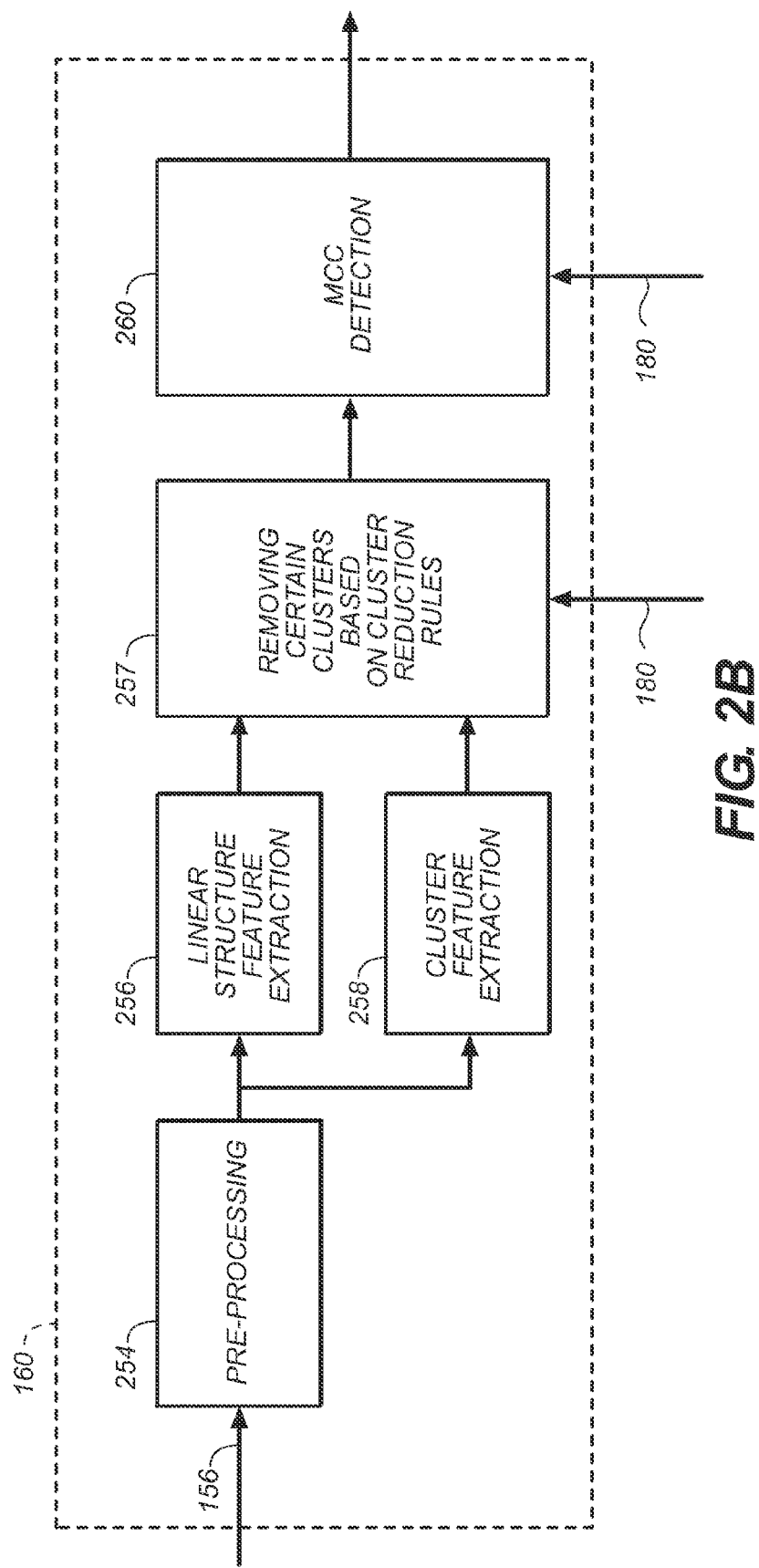

In general, the configurable detection system can be configured differently in a workflow (or equivalently, configured for forming different workflows). Exemplary workflows of configurable MCC detection process 160 are depicted in FIGS. 2A and 2B. In FIG. 2A, mammographic test images 156 are first processed in a pre-processing step 254 which applies various image processing algorithms to the incoming images to form microcalcification candidate clusters that can be tested for cancerous lesions. This includes processes such as filtering, morphological processing, and spot feature extraction, for example.

Exemplary spot features may include any of the following as well as other features:
Density features, characterized by statistics of gray levels, such as mean, minimum, maximum of pixels on a spot;
Boundary or margin features, characterized by gradient calculated on the spot boundary;
Morphological features, such as shape and size; and
Texture analysis, basically using a statistical approach to characterize the stochastic properties of the spatial distribution of gray levels in an image; specifically, the entropy and homogeneity are calculated.

For a first exemplary workflow of microcalcification detection shown in FIG. 2A, the microcalcification candidate clusters enter a linear structure feature extraction step 256 and a cluster feature extraction step 258 followed by an MCC detection step 260 that classifies microcalcification candidate clusters into malignant or benign types. Certain MCC detection parameters are supplied by the step of MCC detector training system 180, to be discussed subsequently. Cluster feature extraction is also to be discussed for the step of MCC detector training system 180. Linear structure feature extraction is also explained in more detail in subsequent discussion.

For a second exemplary workflow of microcalcification detection shown in FIG. 2B, the microcalcification candidate clusters enter linear feature extraction step 256 and cluster feature extraction step 258, followed by a reduction step 257 for removing certain clusters based on cluster reduction rules. The remaining MCC candidate clusters, after step 257, enter MCC detection step 260 that classifies microcalcification clusters into malignant or benign types. Candidate cluster removing rules and certain MCC detection parameters are supplied by processing in MCC detector training system 180.

Figure 3A:
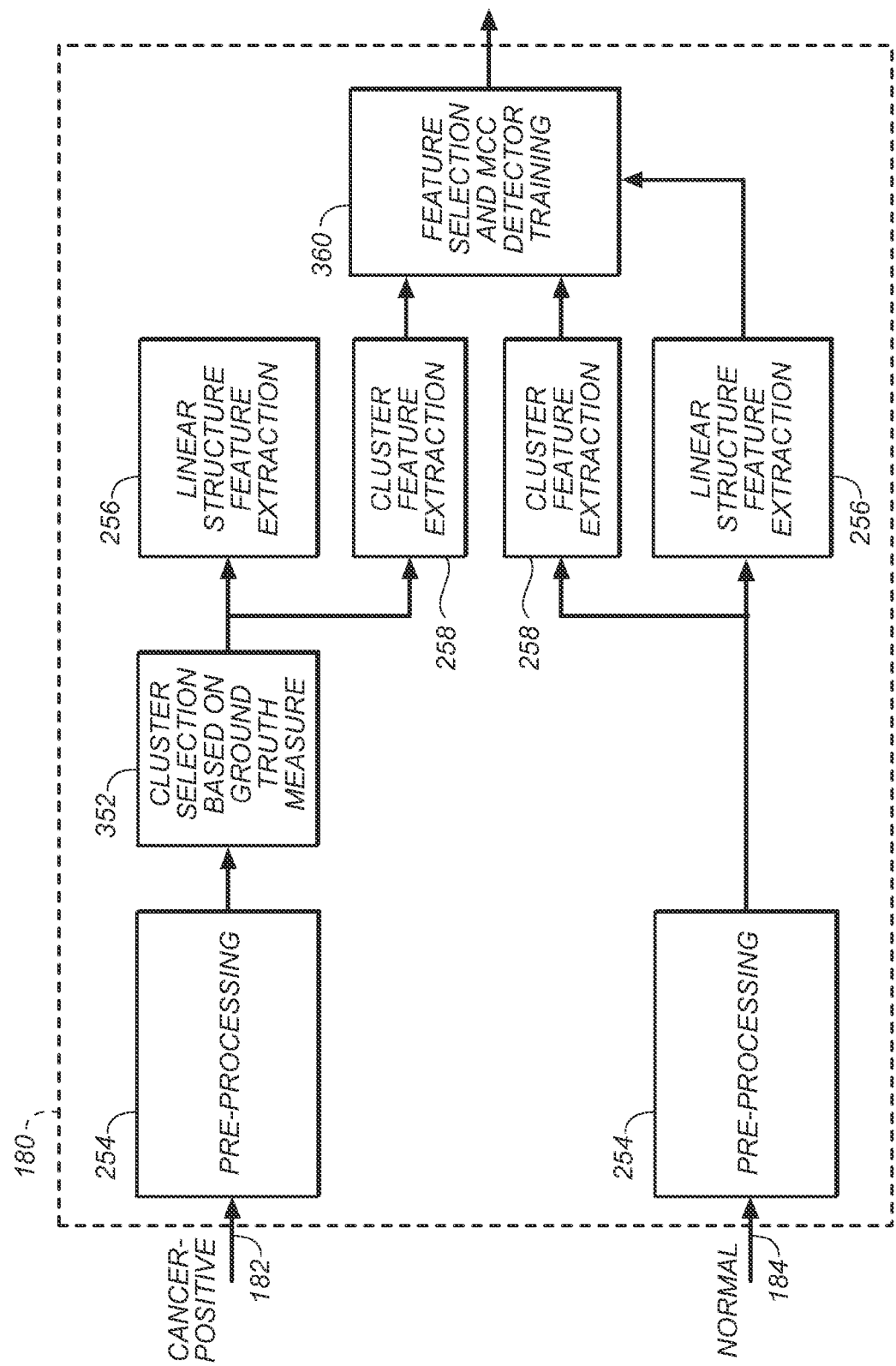
FIGS. 3A and 3B show exemplary workflows for MCC detector training for the current invention.

FIG. 3A depicts an exemplary workflow of MCC detector training system 180. A plurality of normal (non-cancerous) mammographic images 184 are processed in pre-processing step 254 which applies various image processing algorithms such as filtering, morphological processing, and spot feature extraction, for example, to the incoming normal images to form normal clusters. Following pre-processing step 254, the image data for images 182 are processed in a cluster selection step 352, based on ground truth measure. The ground truth measure provides an indication of the degree of importance or involvement of a cancerous mammographic image or a true MCC cluster in MCC detection training. In embodiments of the present invention, a ground truth measure may be represented by different tests. One exemplary test is the number of true MCC clusters that are enclosed within the ground truth region that is defined by a radiologist. These clusters are processed in linear structure extraction step 256 and cluster feature extraction step 258 where linear structure features and cluster features are extracted. Similar to the categories of spot features, exemplary cluster features may include density features, boundary features, morphological features, texture features, and distribution features, among others. Exemplary linear structure features are discussed in more depth subsequently. A feature selection and MCC detector training step 360 is described in more detail subsequently.

Referring back to FIG. 3A, features extracted in steps 256 and 258 are input for evaluation to a feature selection and MCC detector training step 360. Since each feature has been carefully chosen to separate cancer cases from normal cases, it is reasonable to expect that there will be some separation in feature space between a set of normal candidates and a set of cancer candidates. Exemplary requirements state that the linear separation of each feature be at least 55%, which means that 55% of candidates, or other suitable threshold percentage of candidates, be classified correctly with a linear classifier. The exemplary requirement leads to a single alternative: to use a linear classifier to evaluate the features. One alternative for a linear classifier is to assume a Gaussian distribution (with equal variances) and construct a classifier under this assumption. This alternative uses logic described in numerous basic statistics texts, such as for a linear discriminator classifier, for example, and allows relatively straightforward implementation.

In general, feature selection and detector training involve manual operations. The viewer typically select or de-select features from a list. The updated feature list is automatically saved and can be compared to other feature sets by classifying with a linear classifier or Neural Network (NN). The viewer also has the ability to view histograms of each feature and scatter plots of features (in 2 dimensions), comparing cancerous lesions and normal areas, which also helps in assessing the relative quality of features.

One alternative is to automatically analyze the features, selecting the best combination. A disadvantage of this approach is that there may be no clear method to determine what the best combination of features might be. First, criteria is defined (most likely including a classification or distance metric, separating normal regions from cancerous lesions). Secondly, a systematic procedure to combine features is defined. At the extreme, every combination of n features can be processed. However, this may be very time consuming depending on the criteria. Another option is to start with an empty set of features and iterate, adding the 'best' feature at each iteration until the criteria metric no longer improves.

Here, detector training refers to the process involving 'training' data (a subset of the overall data that have been determined as normal or cancerous) which are selected features. In the case of NN logic, training involves using the training data to tune the NN's weights.

A NN can be described as a system of weights connected by non-linear activation functions. The activation function is usually a "squashing" function, such as a hyperbolic tangent, which forces all inputs to the range of (−1,+1). To train, the NN uses the true class of each candidate to compute an error function. For example, the square error is the square of the difference between the output of the NN and the true class of the candidate. In the worst case, the square error is 4 and in the best case the square error is 0. Each candidate is processed through the NN and the error is computed. The error is then fed back through the network and each weight is updated in a manner that reduces the error. The degree to which each weight is adjusted is determined by a user parameter called the learning rate, which scales the weight update factor. The viewer also decides on the overall size of the NN, which in turn determines the degree of complexity of the NN.

In the end, several parameters of the NN can be adjusted (such as the error function, the activation function, and the update procedure, for example), but the two mentioned earlier (learning rate and size) are the most noted. The NN learning level can be evaluated by plotting the mean square error (MSE) of all the candidates as the NN is trained. Given a subset of candidates that is not used to train, but is evaluated each iteration, the viewer can observe how well the NN generalizes to new data. Generally, in a well trained NN, the test or evaluation data's MSE follows the training MSE closely. The test MSE will tend to be greater than the training MSE, but the relative closeness of the two is more important. As these diverge, it indicates that the NN is memorizing the training data.

Referring back to FIGS. 1, 2A, and 2B, a trained MCC detector in system 180 is used in detection process 160 for MCC detection. The dashed arrow from system 180 to detection process 160 in FIG. 1 indicates that there is no "on-line" connection between system 180 and detection process 160. System 180 processing is performed "off-line". The feature selection and NN structures and parameters learned in system 180 are used/implemented exactly in detection process 160 (more precisely, in step 260 in FIGS. 2A and 2B).

Figure 3B:
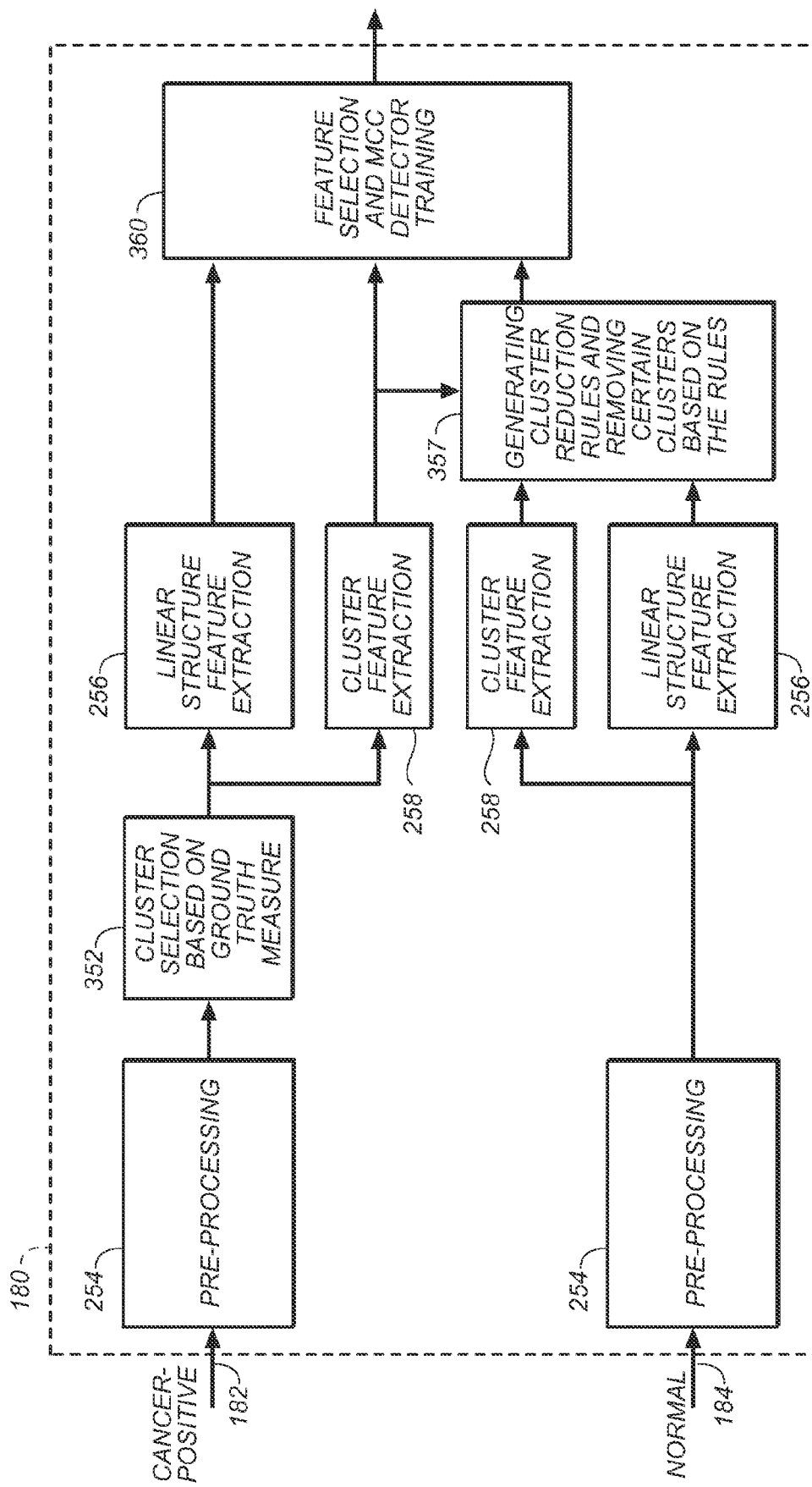

In the logic flow of FIG. 3B, different handling is provided for non-cancerous normal mammographic images 184. FIG. 3B depicts another exemplary workflow of MCC detector training system 180. The basic structure in this exemplary workflow is the same as that shown in FIG. 3A, except that a certain number of normal clusters are potentially removed in a step 357 before step 360. These removed, potentially normal clusters are confirmed to be associated with linear structures based on the cluster reduction rules in step 357. It is known to those skilled in the diagnostic imaging arts that the majority of clusters that are associated with linear structures are non-cancerous. Removing the clusters that are associated with linear structures can improve the performance of feature selection and MCC detector training in step 360. The cluster reduction rules are discussed in more detail subsequently. The alternative workflow shown in FIG. 3B provides necessary information for the MCC detection workflow displayed in FIG. 2B.

Curvilinear features projected in the mammogram can be from blood vessels, lactation ducts, ligaments of the breast, and other generally curvilinear structures. The curvilinear structure is a net of massive and complex curvilinear markings on a given mammogram. Due to the projection of the three-dimensional breast onto a two-dimensional mammogram, different parts of the curvilinear structure may have different appearance with varying widths, varying lengths, and different contrast relative to the surrounding breast tissue. The option of pre-classification global mask generation to extract curvilinear structure may be of limited value because global curvilinear marking of structures and accurate mask extraction is not a simple task. Global masking tends to extract only small portion of linear structure or to extract an excessive number of "lines".

Vascular lines are large calcified blood vessels on a mammogram. Microcalcifications are bright spots on the mammogram and, as noted earlier, can be the primary early signs of breast cancer. Microcalcification spots usually appear in clusters, and malignant microcalcification spots usually have irregular shapes.

An alternative, after forming MCC candidate clusters in step 254 in FIGS. 2A and 2B, is to identify linear structures only in the neighborhood where the MCC candidate clusters reside. For each of the candidate clusters, a region of interest (ROI) is defined that encloses the MCC candidate spots of each of the MCC candidate clusters. An MCC candidate spot is a spot contained in the MCC candidate cluster that is under testing for cancerous lesions. A linear structure identification procedure is applied to a small region (ROI) centered around each MCC candidate cluster to minimize unwanted influence from other breast tissue. This reduces processing time since the number of MCC candidate clusters is limited and only a small portion of the breast area needs to be processed, in comparison to a global line mask approach. Such an alternative is applicable to the process shown in FIGS. 3A and 3B.

Figure 4:
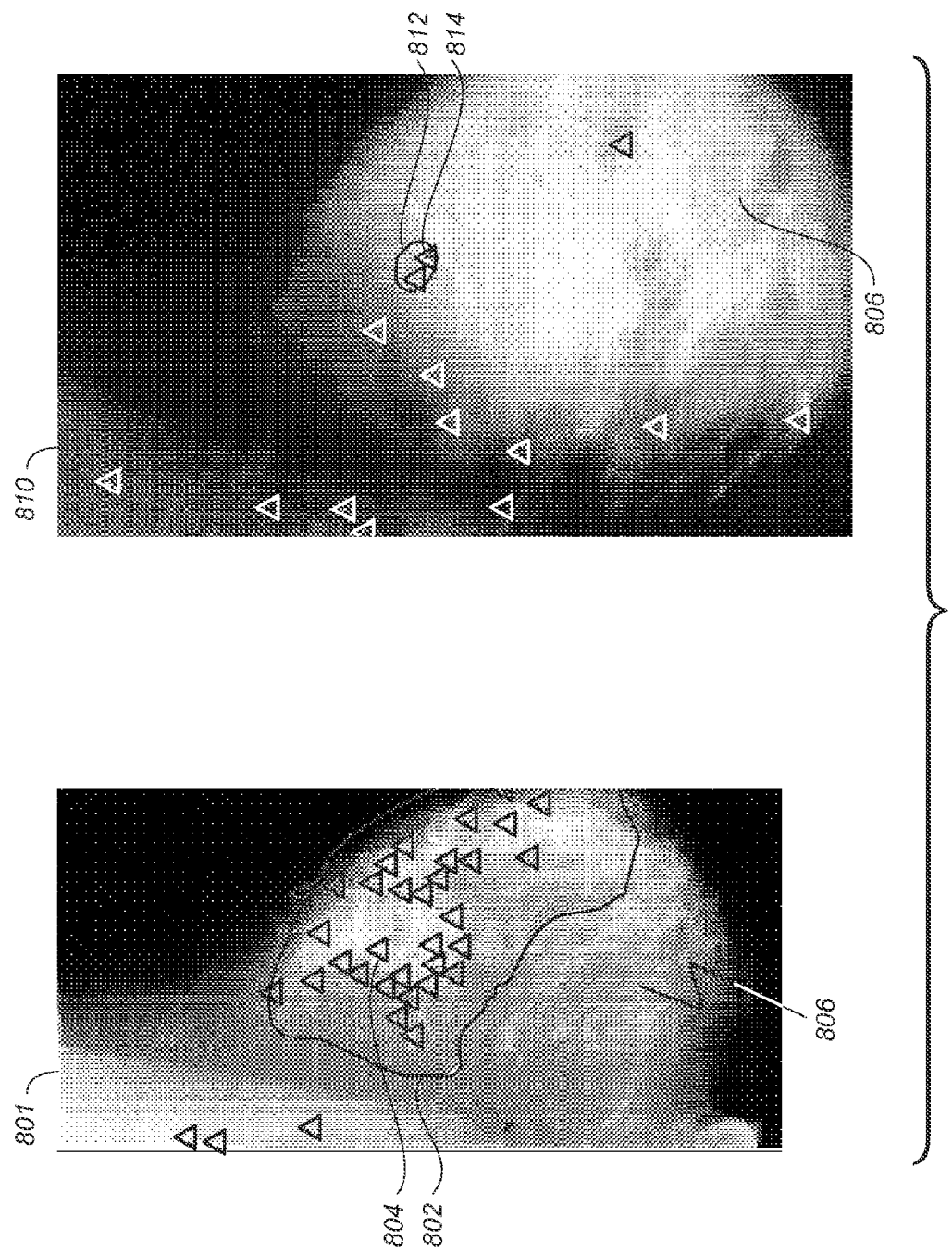
FIG. 4 is an illustration of mammographic images with MCC ground truth indicated.

Referring to FIG. 4, there are shown two cancerous mammographic images 801 and 810. In image 801, clusters 804 that are enclosed by a boundary 802 are true MCC clusters that have been verified by a radiologist. In this example, the region that is enclosed by boundary 802 is a ground truth region. For image 801, there are nearly 30 clusters inside boundary 802. In image 810, clusters 814 that are enclosed by a boundary 812 are true MCC clusters that are verified by a radiologist. There are only 2 clusters inside boundary 812. Those skilled in the art understand that if clusters 804 and 814 are all included in a detector training process, with a high probability, the detector will be trained in favor of the type of image 801, simply because clusters 804 greatly outnumber clusters 814.

Therefore, to reduce MCC detector training bias, embodiments of the present invention use a ground truth measure that tests the number of true MCC clusters that an image contains. If an image contains less than or equal to N true MCC clusters, these true MCC cluster are all used in detector training. If an image contains more than N true MCC clusters, randomly (or with some criteria, such as using a cluster ranking) choose up to N (including zero) true MCC clusters in the image for detector training. In other words, if a cancerous mammographic image contains too many true MCC clusters, randomly remove a certain number of true MCC clusters and use the remaining true MCC clusters in the MCC detector training process. In some cases, even the image itself could be removed. An exemplary value for N could be 4 in one embodiment.

Another exemplary test for ground truth measure is the ratio of ground truth region size to the size of the breast in a mammographic image. Referring to images 801 and 81, in FIG. 4, the ratio of ground truth (inside boundary 812) size to the size of the breast 816 is much smaller than the ratio of ground truth (inside boundary 802) size to the size of the breast 806.

If this size ratio for an image is smaller than or equal to a value M, the true MCC clusters in the image are all used in MCC detector training. If the size ratio for an image is larger than value M, randomly (or with some criteria, such as using cluster ranking) choose up to N (including zero) true MCC clusters in the image for MCC detector training. An exemplary value for M could be 0.1.

Figure 5:
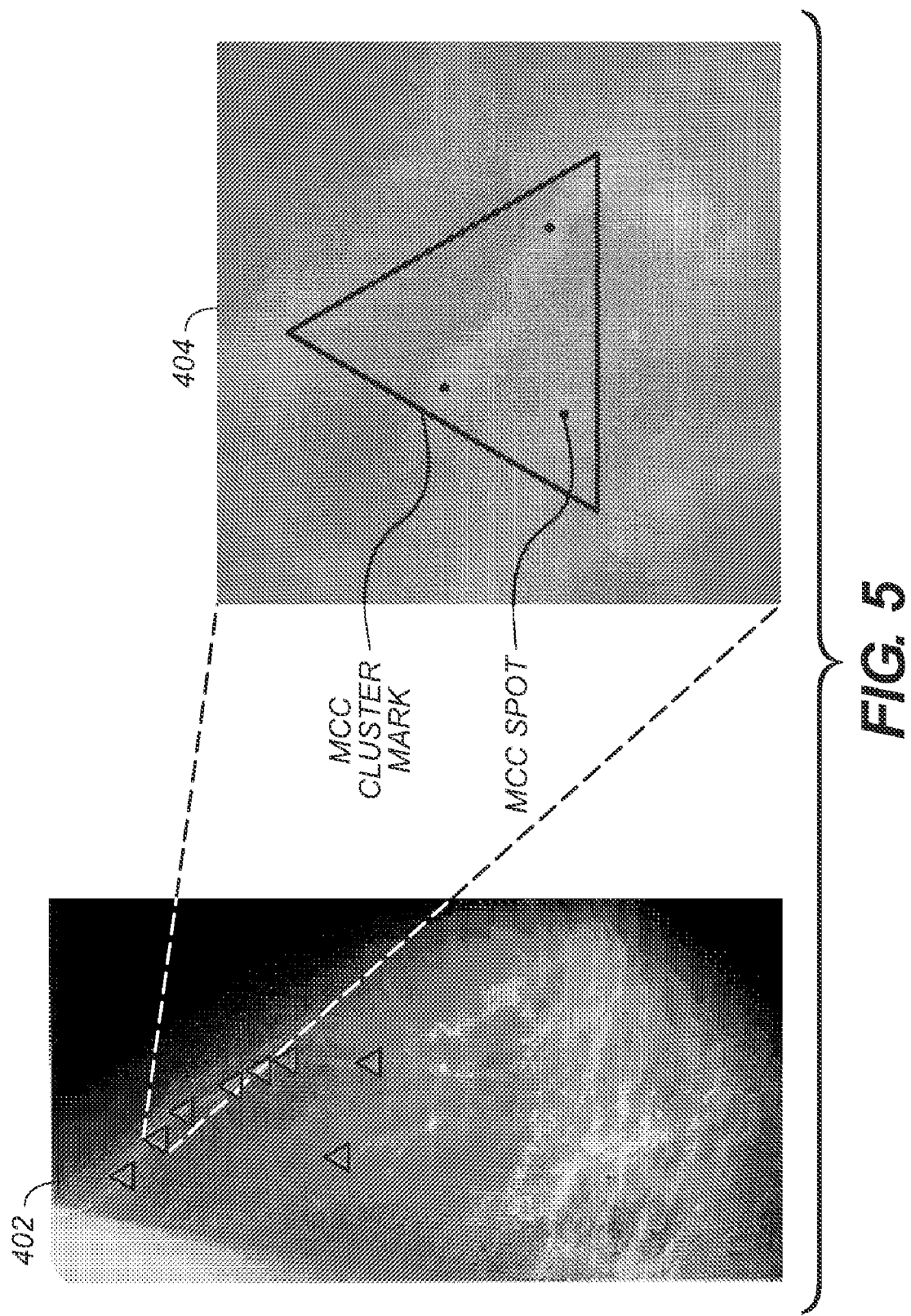
FIG. 5 is a graph illustrating exemplary MCC candidate clusters in a mammogram.

FIG. 5 shows an exemplary mammogram 402 with small triangles that indicate the MCC candidate clusters identified in the pre-processing state. On the right side in FIG. 5 is an enlarged image of the region of interest (ROI) 404 that contains one of the MCC candidate clusters.

The method of microcalcification detection in mammographic images in an embodiment of the present invention employs several identifiable features that are extracted from the gradient magnitude domain and Hough parameter domain. The following describes the linear structure feature extraction that is used in step 256 in FIGS. 2A through 3B.

Features of Ensemble Average of Lines in Gradient Magnitude Domain

Figure 6:
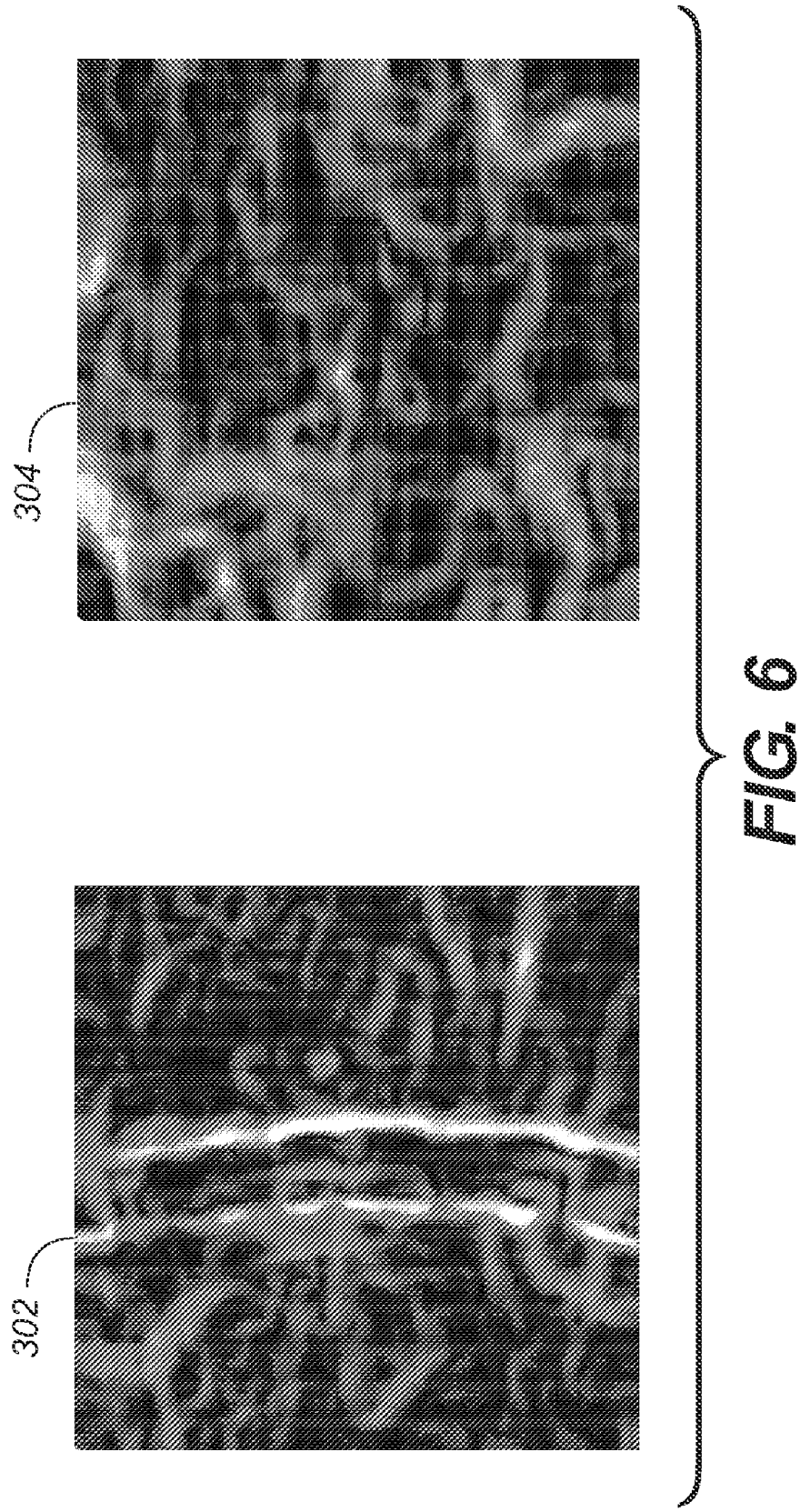
FIG. 6 is an illustration of exemplary regions of interest in the gradient magnitude space.

In linear structure feature extraction step 256 an intensity imaging domain ROI 404 as in FIG. 5 is transformed to a gradient magnitude domain, or gradient imaging domain, ROI (gROI). One benefit of working in the gradient magnitude imaging domain is that statistics gathered from the gROI are essentially intensity-invariant. FIG. 6 displays a few exemplary gROIs 302 and 304 used in the present algorithm. Noted that the position and size of an ROI are determined by the positions of the underlying MCC candidate spots that the cluster contains.

The linear structure identification process starts with extracting information from a rotatable band that covers all or part of candidate spots in the MCC candidate cluster under investigation. The rotatable band comprises a plurality of gROI image pixels. The plurality of gROI pixels change as the rotatable band rotates around the geometric center of the band. The mathematical derivation of the rotatable band for one exemplary embodiment is given next. Note that variations and modifications to this sequence can be effected by a person of ordinary skill in the art without departing from the scope of the invention.

Figure 7A:
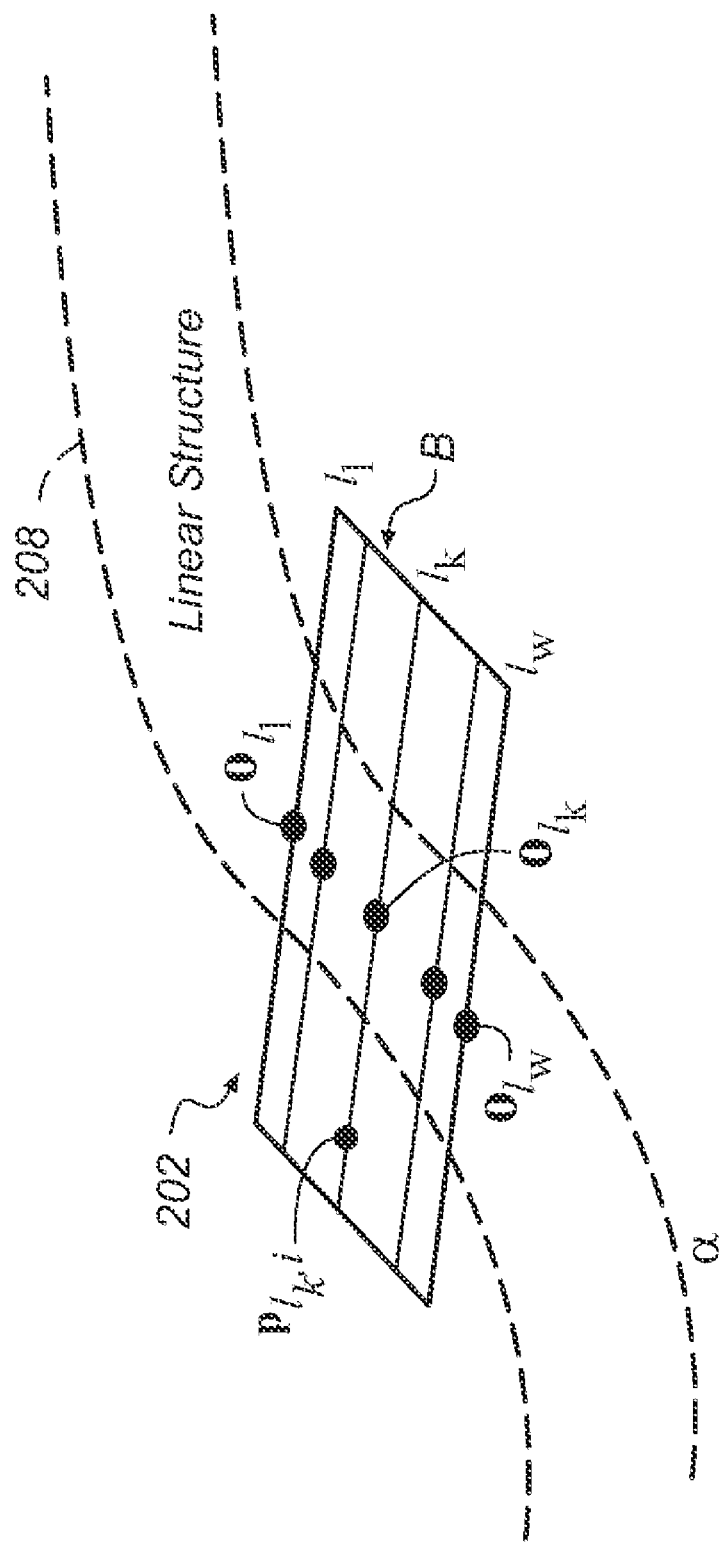
FIG. 7A shows how a rotatable band is used to identify a linear structure in one embodiment.
Figure 7B:
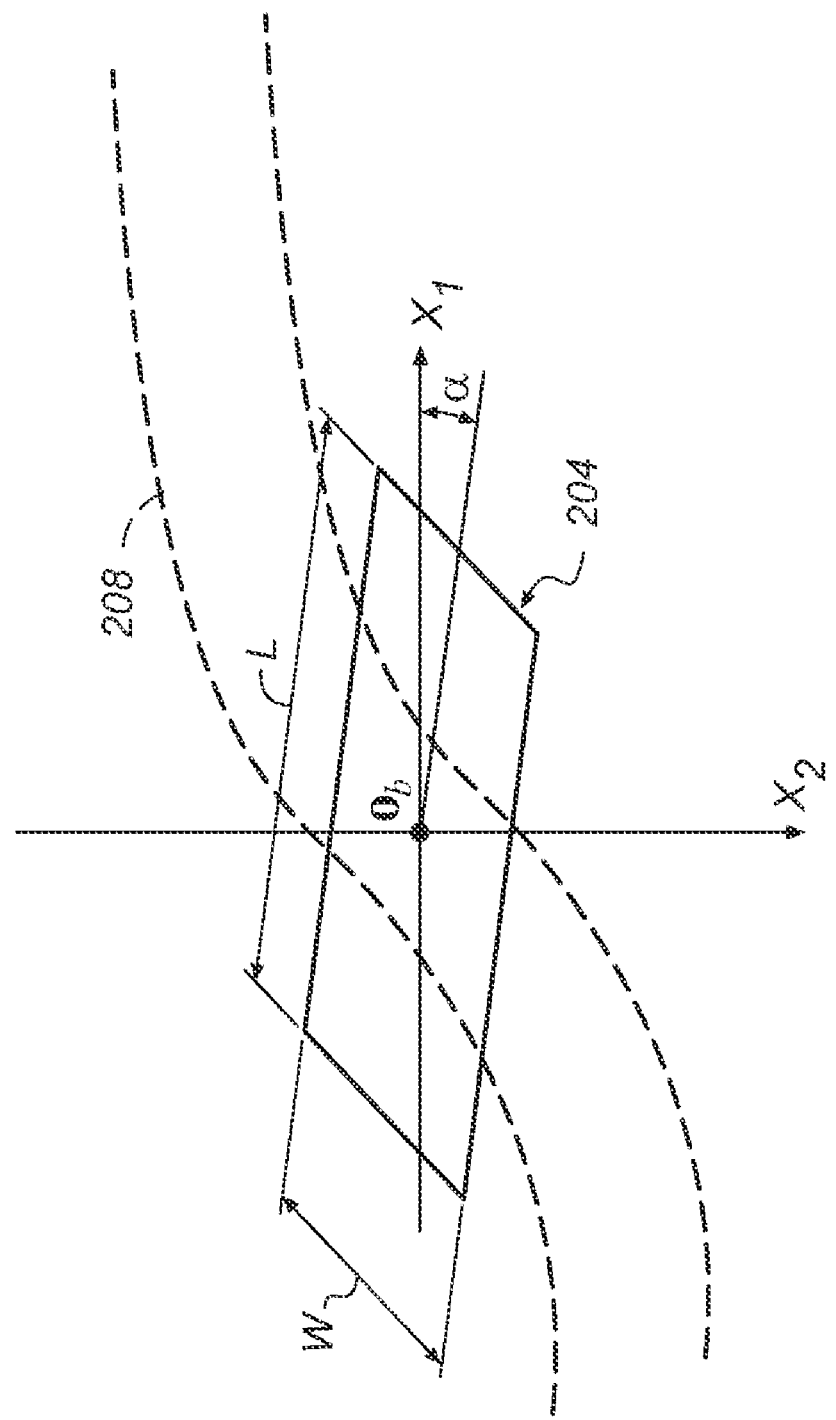
FIG. 7B shows additional detailed information about how the rotatable band is used.

FIG. 7A shows a sketch 202 of a linear structure 208 and a rotatable band. FIG. 7B shows additional details. Define the band center $o_b$ as the origin of a local coordinate system ($X^1$, $X^2$) (in a sketch 204 of FIG. 7B) whose axes are parallel to the image (gROI) coordinate system axes. Angle $\alpha$ determines the band orientation with respect to the local coordinate system.

Denote the rotatable band by $B(\alpha)$ that contains W lines $l_k(\alpha)$:

$$B(\alpha) = \{l_k(\alpha)\}, k \in [1, \ldots, W] \quad (1)$$

Denote the line center of line $l_k(\alpha)$ by $o_{l_k}$. Denote a pixel on line $l_k(\alpha)$ by $p_{l_k,i}(\alpha)$. Line $l_k$ is a collection of pixels:

$l_k = \{\hat{I}(p_{l_k,i}(\alpha))\}, i \in [-(L-1)2, \ldots, (L-1)/2]$, L is the line length. Here $\hat{I} = |\nabla I|$ is the gradient magnitude domain image (gROI) derived from the intensity domain image (ROI) denoted by I. In the sketch 204 displayed in FIG. 7B, the band is in a position where lines $l_k$ are approximately perpendicular to the medial axis of the linear structure. For notational simplicity, parameter $\alpha$ is omitted in some of the expressions in the following discussions.

Denote an ensemble average of the set of lines $\{l_k\}$ in the band by $s(\alpha)$ with elements $s_i(\alpha)$: $s(a) = \{s_i(a)\}$, where $$s_i = \frac{1}{W} \sum_{k=1}^{W} \hat{I}(p_{l_k,i}) \quad (2)$$

Referring back to FIG. 7A, the pixel coordinate $p_{l_k,i}$ can be computed as $p_{l_k,i} = if_l + o_{l_k}$; where the centers $o_{l_k}$ are obtained using $$o_{l_k} = kf_b + o_b; k \in [-(W-1)/2, \ldots, (W-1)/2;]$$

$$o_b = \begin{bmatrix} o_b^{x1} \\ o_b^{x2} \end{bmatrix}; f_b = \begin{bmatrix} f_b^{x1} \\ f_b^{x2} \end{bmatrix} = \begin{bmatrix} \sin(\alpha) \\ \cos(\alpha) \end{bmatrix};$$

$$o_{l_k} = \begin{bmatrix} o_{l_k}^{x1} \\ o_{l_k}^{x2} \end{bmatrix}; f_l = \begin{bmatrix} f_l^{x1} \\ f_l^{x2} \end{bmatrix} = \begin{bmatrix} \cos(\alpha) \\ -\sin(\alpha) \end{bmatrix}.$$

The bands $B(\alpha)$ at different angles are not extracted through the conventional method of interpolation but through a simple sampling procedure that is quite adequate for the present application.

Various linear structure features can be generated from the processing of the bands. Two main features are introduced in the present invention. One of the features is a maximum relative magnitude of the ensemble average curves. The relative magnitude of the ensemble average curve of a set of lines in the band at a particular angle is simply defined as $$\Psi(\alpha) = \max(s(\alpha)) - \min(s(\alpha)) = \max_i(s_i) - \min_i(s_i).$$

In practice, angle $\alpha$ is chosen at a few discrete orientations. Therefore, the relative magnitude of the ensemble average curve can be expressed as $\Psi(\alpha_j) = \max(s(\alpha_j)) - \min(s(\alpha_j))$; $j \in [1, \ldots, N_\alpha]$. It can be further simplified as $\Psi_j = \max(s_j) - \min(s_j)$; $j \in [1, \ldots, N_\alpha]$.

The maximum relative magnitude of the ensemble average curve is then obtained as $$\Psi = \max_j(\Psi_j). \quad (3)$$

Accordingly, band $B_j$ that produces maximum relative magnitude is denoted by $B_\Psi$.

With the relative magnitude of the ensemble average curve, another feature, ensemble average ratio $\Re$ can be computed as:

$$\Re = \max_j(\Psi_j) / \min_j(\Psi_j). \quad (4)$$

It can be seen that if an MCC candidate cluster is not associated with a linear structure the ensemble average ratio $\Re$ is close to 1, which signifies the 'isotropic' nature of the underlying structure measured by using the ensemble averaging. On the other hand, if an MCC candidate cluster is associated with a linear structure the ensemble average ratio $\Re$ moves away from 1, which signifies the 'anisotropic' nature of the underlying structure.

Features in Hough Transformation Domain

Two features from the Hough Transformation domain are used in the linear structure identification process in an embodiment of the present invention. The Hough Transform maps points on a line in Cartesian space to curves (sinusoids) in the Hough parameter space. Points that are collinear in the Cartesian space generate curves that intersect at a common point (forming a peak in the Hough parameter space).

Referring again to FIG. 7A, each point $p_{l_k,i}$ in band $B(\alpha)$ that has a Cartesian coordinate is transformed into a discretized $(r,\theta)$ curve in Hough parameter space; where r is the length of a normal from the origin to line in band $B(\alpha)$ and $\theta$ is the orientation of the normal with respect to the $X^1$ axis.

For the exemplary gROI 302 that was shown earlier in FIG. 6, there are two high peaks in the Hough parameter accumulator array indexed with discretized r and $\theta$. These two peaks will appear approximately at the same angle $\theta$ but at different r lengths. It is therefore a feature (or measure) of "angle spread" $\delta_\theta$ is defined as following.

Denote the Hough peak array by $H=\{h_{i,j}\}$ and its corresponding angle array by $\Theta=\{\theta_{i,j}\}$; where $i\in[1, \ldots, N_r]$; $j\in[1, \ldots, N_\theta]$. $N_r$ is the number of quantized length intervals and $N_\theta$ is the number of quantized angle intervals.

Collect a subset $H^s=\{h_{i,j}^s\}$ of H; the elements $h_{i,j}^s$ all have values above $N$ percent of the highest peak value in H. Corresponding to the subset $H^s$, there is a subset $\Theta^s=\{\theta_{i,j}^s\}$ of $\Theta$. The angle spread $\delta_\theta$ can be readily computed as:

$$\delta_\theta = |\max_s(\Theta^s) - \min_s(\Theta^s)|. \quad (5)$$

It is obvious that if there are parallel thin lines presented in a band $B(\alpha)$, the angle spread $\delta_\theta$ for that band is zero or close to zero. On the other hand, if random structures are presented in a band $B(\alpha)$, the angle spread $\delta_\theta$ will be large.

Another feature from Hough space is the normalized maximum Hough peak that is simply defined as $$\varphi_h = \max_{i,j}(h_{i,j}^s) / \text{sum}(h_{i,j}). \quad (6)$$

Additional Measure for TP Protection

It has been observed that some of the true (i.e. malignant) MCC clusters may reside in an area where linear structure-like objects are present and can be verified as FPs. It has also been observed that true MCC clusters may have topological ring-like structures surrounding some of the spots. This is shown, for example, in a gROI 210 in FIG. 8, with spots 308. A method is then used to take advantage of the ring structure in a cluster in order to identify true MCC clusters.

Using an MCC candidate spot as the origin, perform a search along a ray that radiates from the origin until the ray hits the ring or reaches a predefined distance without a hit. The search process can be formulated as following (referring to a graph 212 in FIG. 8).

Denote a ray by $R_{k\beta}$ and its opposite ray by $R_{k\beta+\pi}$, where $\beta=\pi/N_R$; $k\in[1, \ldots, N_R]$. $N_R$ is a positive integer greater than one. Denote a hit array by $T=\{t_k\}$. The array elements $t_k$ are initialized as zero. Only if both $R_{k\beta}$ and $R_{k\beta+\pi}$ hit a ring, the corresponding array element $t_k$ is set to one; otherwise, the corresponding array element $t_k$ remains zero.

A simple measure is therefore defined as the sum of hits $\xi_t$ that a hit array has. This measure is simply computed as $$\xi_t = \sum_k t_k. \quad (7)$$

Cascade Rule Based Linear Structure Classification

Referring back to FIG. 3B, the features described in the above sections are not only used in MCC detector training step 360 and MCC detection step 260 but are also used in step 257 for removing certain clusters based on cluster reduction rules. Cluster reduction rules are contained in a cascade-rule-based linear structure identification algorithm.

The relative magnitude of the ensemble average curve and the ensemble average ratio are the first two features that are evaluated to identify linear structures. This first evaluation process tags a cluster with a status of (i) being associated with linear structures (LS) (ii) not being associated with linear structures (nonLS); or (iii) uncertain. As a result, any MCC candidate cluster in an uncertain status is further evaluated by the rules that are applied to the features of Hough parameters.

It should be pointed out that the first evaluation operation on ensemble averages is, in general, not orthogonal to the second evaluation operation on the Hough parameter in the present application. In other words, these two operations may explore the same underlying evidence to support the linear structure classification process. However, in terms of computational complexity, the computation of ensemble averaging is linear, while Hough Transformation is nonlinear. Also, the execution of ensemble averaging of lines is performed at multiple angles. The Hough Transform is performed at a single angle position that is determined by the first evaluation operation of ensemble averaging of lines in the rotatable band.

The above discussed algorithm is summarized below. The paragraphs following the algorithm summary explain the workings of the algorithm:

```
for each clst do
    gROIgnrt(clst,img,gROI);
        for each α_j where j∈[1,...,N]do
            bandXtrct(clst,gROI,B_j,α_j);
            bandPfling(B_j,s_j)
        end
        profileFeatureXtrct(∀s_j,ψ,ℜ); where j∈[1,...,N]
        apply ProfileRules (clst,ψ,ℜ);
        if status( clst ) == uncertain
            bandHoughTrnsfm(B,H,Θ);
            HoughFeatureXtrct(H,Θ,δ_Θ,φ_h);
            applyHough Rules(clst,δ_Θ,φ_h);
        end
        if status( clst ) == LS
            ringHitChk(clst,gROI,ξ_t);
            applyRingHitRules(clst,ξ_t);
        end
end
```

Function gROIgnrt(clst,img,gROI) simply crops a region of interest (gROI) from the input gradient magnitude mammogram (img) using the position information of the underlying MCC candidate cluster (clst). The size of the gROI depends on the spread of MCC candidate spots within the cluster.

Function bandXtrct (clst, gROI, $B_j$,$α_j$) further crops a band $B_j$ at angle $α_j$ from gROI. The center of the cropped band is at the geometric center of the spots within the cluster clst. In practice, the shape of a band is a square so that two, not one, ensemble average curves of two sets of lines (with respect to $α_j$ and $α_j+π/2$) can be computed (see Equation 2) using one band.

Function profileFeatureXtrct($∀s_j$,Ψ,ℜ) collects the ensemble averages and computes features (or measures) Ψ and ℜ according to Equations 3 and 4.

Function applyProfileRules(clst,Ψ,ℜ) evaluates Ψ and ℜ with pre-determined boundaries (thresholds) then tags the cluster clst with a number indicating the status as one of the following: (i) LS (associated with linear structure); (ii) nonLS (not associated with linear structure); or (iii) uncertain. Evaluation criteria are described in more detail subsequently.

If a cluster is labeled as 'uncertain', the cluster is further evaluated by first applying a Hough Transform band-HoughTrnsfm(B,H,Θ) to the band and generating a Hough peak array H and an angle array Θ. The band B used in function bandHoughTrnsfm( ) could be the band that generates the maximum relative magnitude of the ensemble average curve in Equation 3, (denoted by $B_ψ$). Or this could be a band having a different (usually larger) size but with the same orientation and center position as $B_ψ$.

Function HoughFeatureXtrct(H,Θ,$δ_Θ$,$φ_h$) executes Equations 5 and 6. Function applyHoughRules(clst,$δ_Θ$,$φ_h$) evaluates $δ_Θ$ and $φ_h$ with pre-defined thresholds and tags the cluster clst with a number indicating the status as 'LS', or 'nonLS'.

If, after evaluating the features of the rotatable bands, a cluster is labeled as LS (associated with linear structure), function rightHitChk(clst,gROI,$ξ_t$) computes $ξ_t$ (see Equation 7) that is evaluated in function applyRingHitRules(clst, $ξ_t$). This basically checks the number of hits that each of the spots has in a cluster and changes the status from LS to nonLS if the maximum number of hits for any one of the spots exceeds a threshold. The purpose of employing function rightHitChk(clst,gROI,$ξ_t$) is to analyze the band and to use function applyRingHitRules(clst,$ξ_t$) to remove the tag LS that is attached incorrectly.

Figure 9:
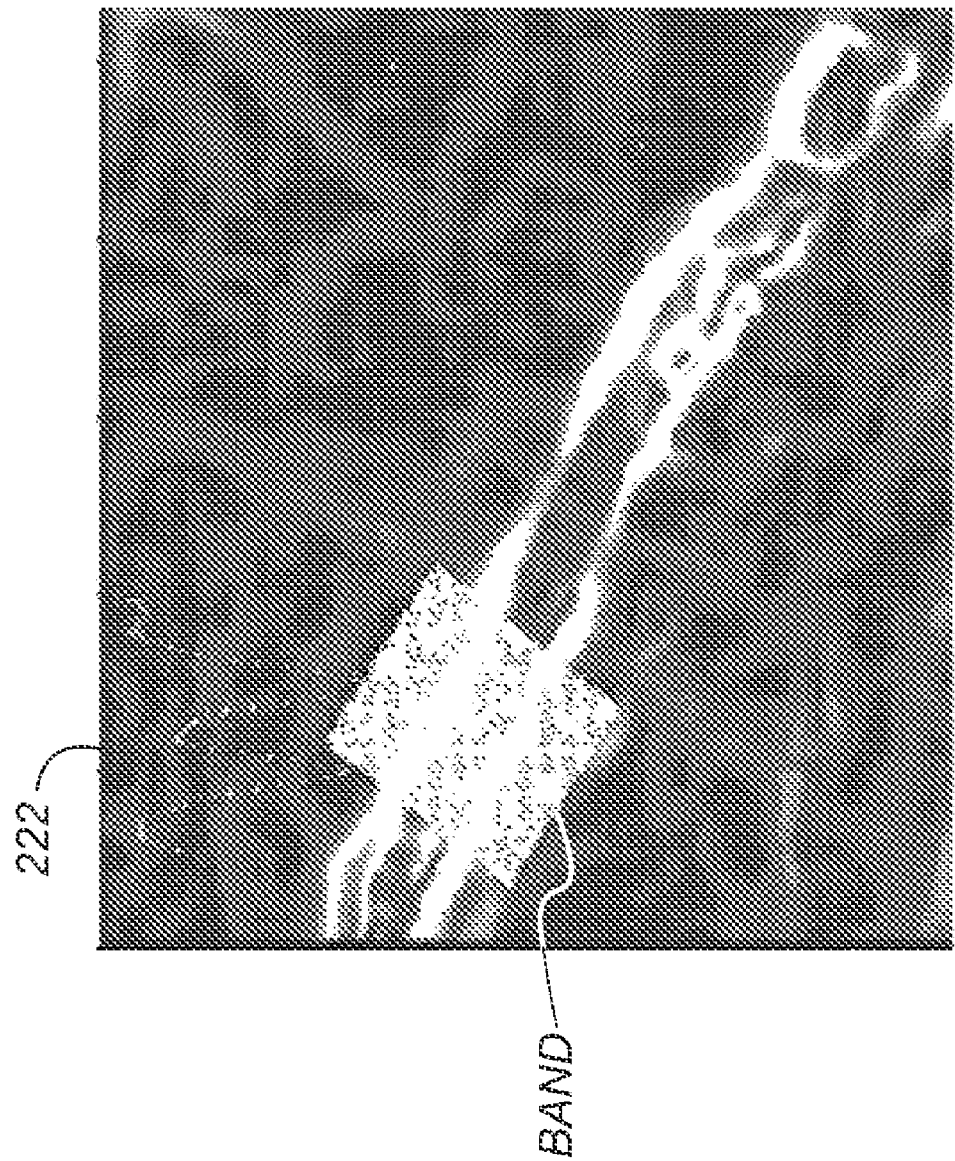
FIG. 9 is an illustration of an exemplary band that covers a blood vessel in a region of interest in a gradient magnitude image.

The cluster reduction algorithm developed in the present invention has been applied to clinical mammograms for assessment. FIG. 9 shows an exemplary band that covers part of a blood vessel in a gradient magnitude image (gROI) 222.

Figure 10A:
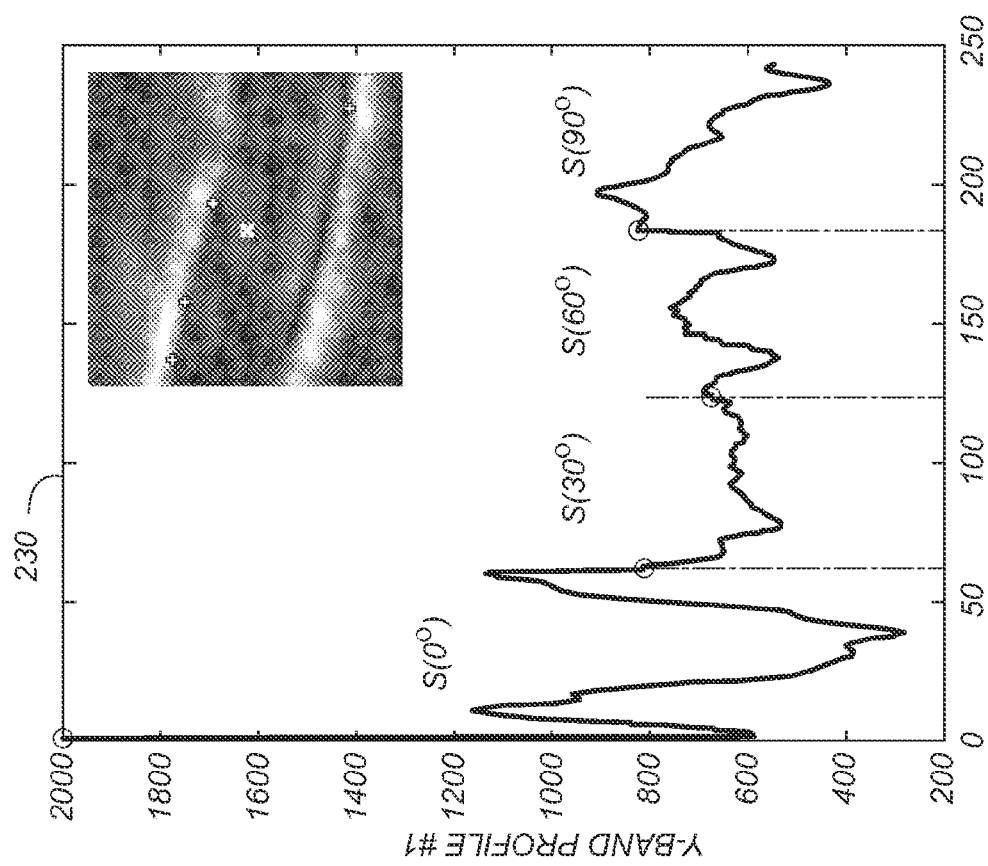
FIG. 10A is a graph illustrating an exemplary curve of ensemble average of sets of lines in a rotatable band when the band is at different angles.

In FIG. 10A, a graph 230 depicts the ensemble averages s(α) of band lines at four different angles for a gROI that has a linear structure. The ensemble average curve s(0°) at 0° has the highest relative magnitude compared to the other three. These four ensemble average curves possess a type of 'anisotropic' characteristic in terms of the relative magnitude. In contrast, the curves in a graph 232 in FIG. 10B display near 'isotropic' characteristics for a gROI that does not have a linear structure.

Figure 11:
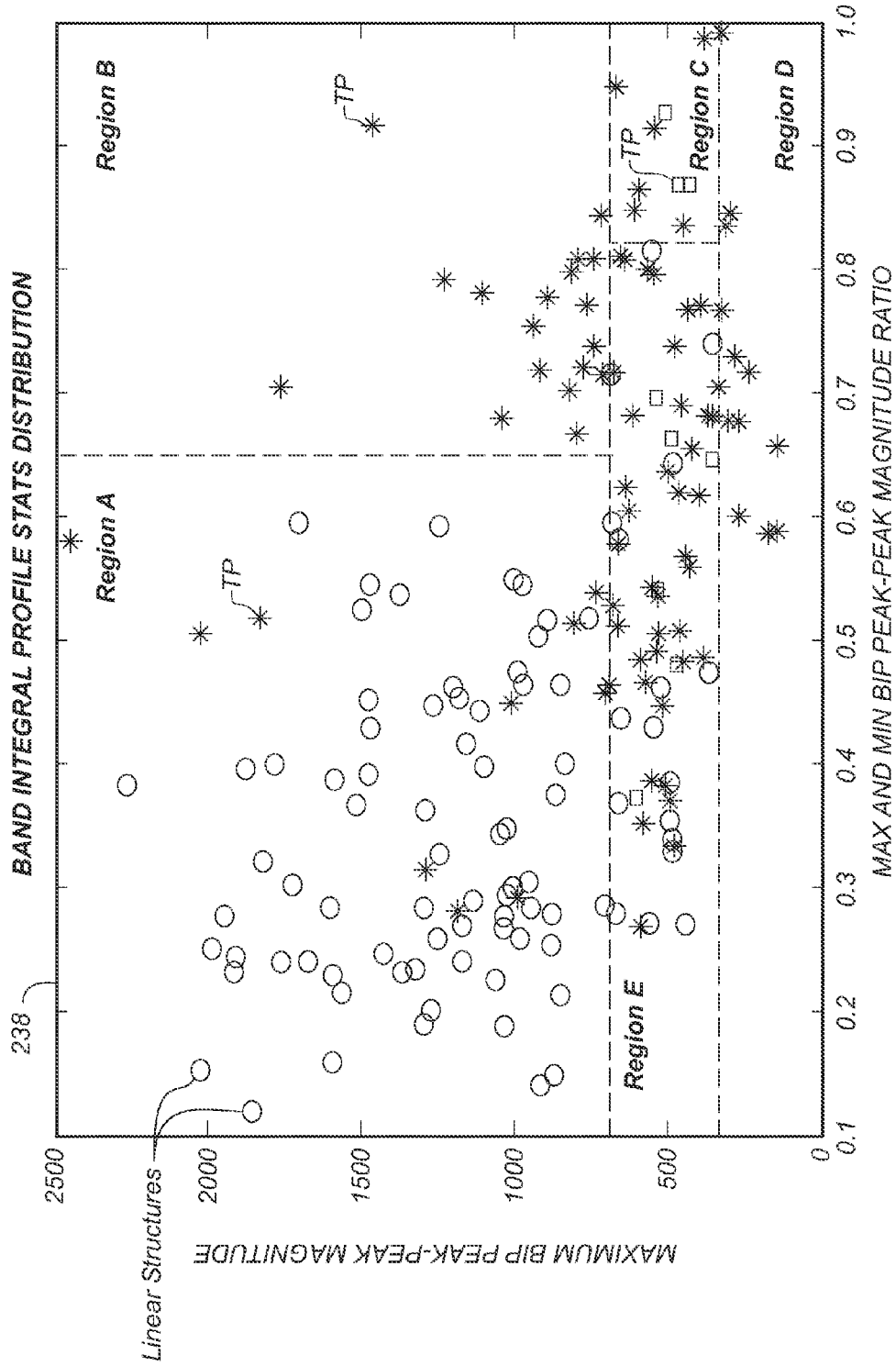
FIG. 11 is a graph illustrating an exemplary distribution of features related to ensemble average of lines.

In FIG. 11 a distribution graph 238 of features Ψ and ℜ is obtained from a number of training cancerous and normal mammograms. This demonstrates that features Ψ and ℜ provide a statistically satisfactory separation for the clusters that have linear structures (LS) and the clusters that are true-positives (nonLS). Although sophisticated algorithms such as SVM could be used to find the feature separation boundaries, the distribution in FIG. 11 is empirically divided into different regions. LS Clusters are concentrated in region A, while nonLS clusters spread mostly in regions B, C and D. Region E contains the clusters with uncertain status. Exemplary rules are devised based on the division of the above regions in the present invention for function apply ProfileRules(clst, Ψ, ℜ). Exemplary predefined thresholding values for Ψ are 700 and 300. Exemplary predefined thresholding value for ℜ is 0.6.

Figure 12:
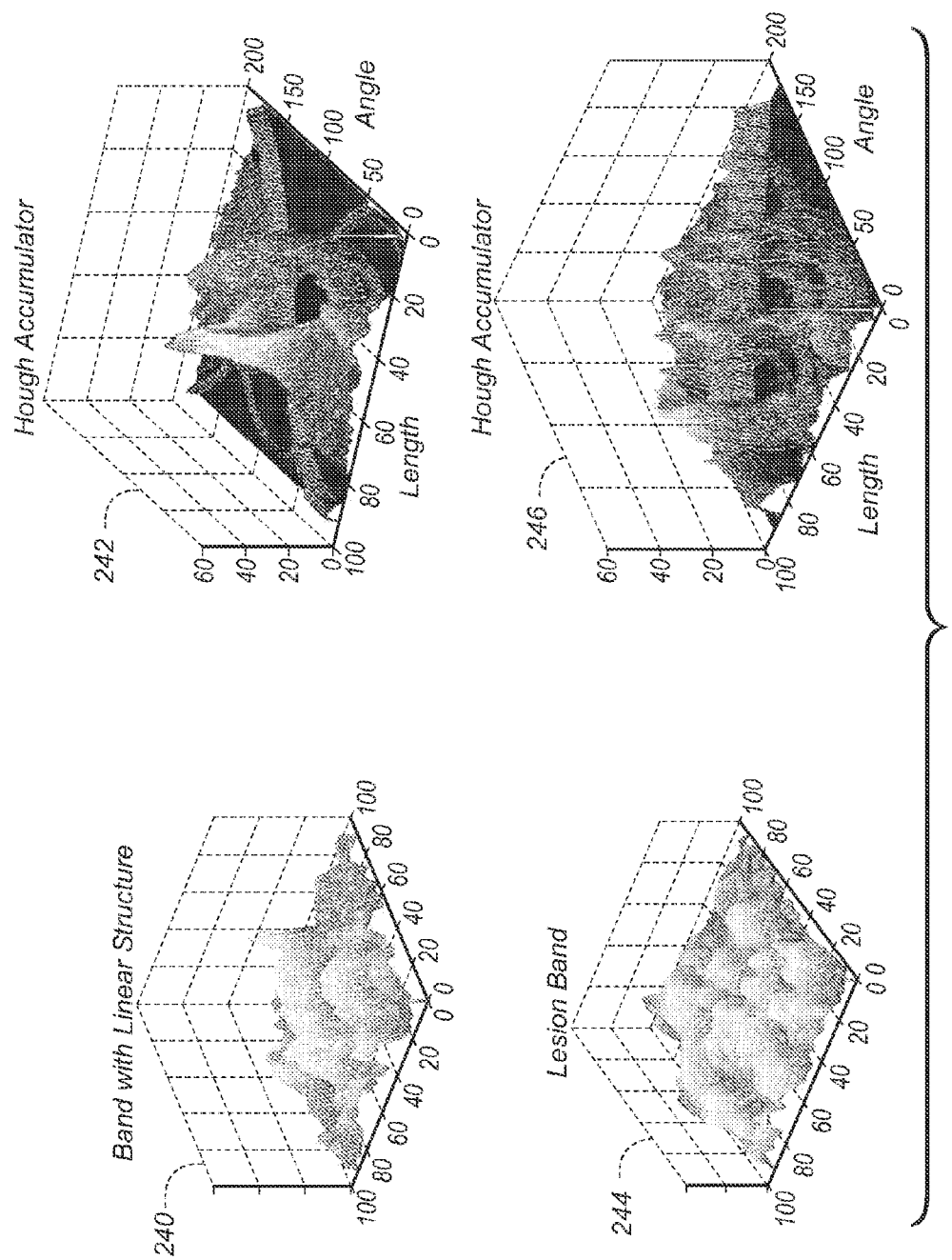
FIG. 12 displays exemplary regions of interest and their corresponding Hough accumulators.

FIG. 12 displays the 3D plot of a band in a graph 240 with linear structures and its corresponding Hough accumulator in a graph 242 plotted with length r and angle θ axes. Set an exemplary ℵ=90. Intuitively, the angle spread $δ_θ$ for the elements $h_{i,j}{}^s$ having values above ℵ percent of the highest peak value is very small. While for the lesion band in ROI 304 in FIG. 6, shown in a graph 244 in FIG. 12, the angle spread $δ_θ$ obviously has a much larger value because of the multiple peaks with similar values sprouted across the angle axis in graph 246 (FIG. 12).

Figure 13:
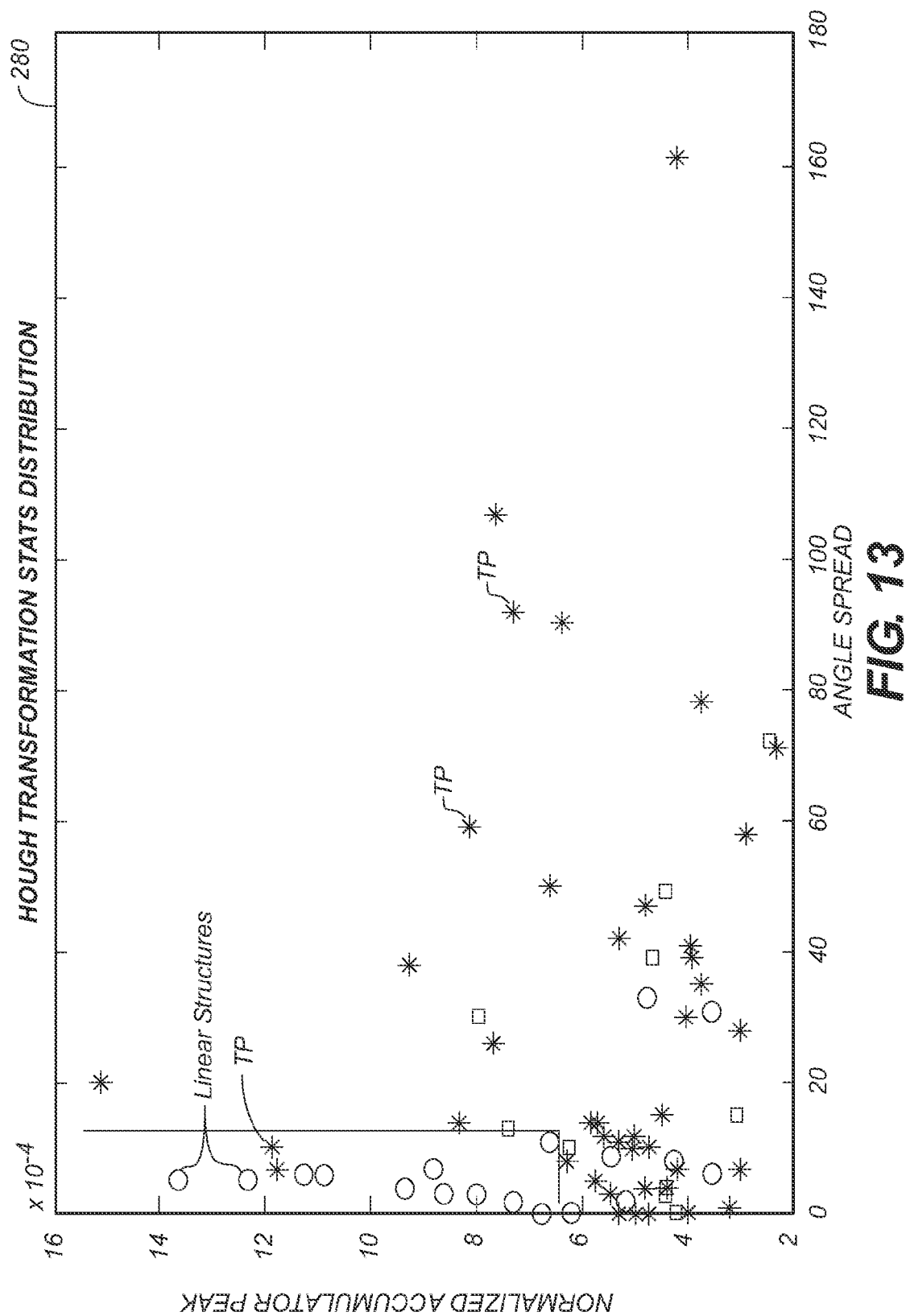
FIG. 13 is a graph illustrating an exemplary distribution of features related to Hough accumulator.

In FIG. 13 a distribution graph 280 of features r and θ also shows a relatively good separation between the LS clusters and nonLS clusters. The solid lines in FIG. 13 provide the empirical thresholds for the execution of function applyHoughRules(clst,$δ_θ$,$φ_h$). Exemplary predefined threshold $δ_θ$ for is 10 and exemplary predefined threshold for $φ_h$ is 0.0005.

It was stated previously with reference to FIG. 1 that linear structure classifier in step 256 could be configured or reconfigured by commands from the human operator, viewer 168 through a command line 174 that is connected to parameter selection step 158. Parameter selection step 158 sends the selected parameters to detection process 160 through path 176. For example, the cluster reduction algorithm can be configured so that a step of true positive protection is activated in the linear structure identification process. Exemplary functions contained in true MCC cluster protection are rightHitChk(clst,gROI,$ξ_t$) and applyRingHitRules(clst,$ξ_t$) that are described previously. The linear structure identification can also be configured so that numerical thresholds can be varied. Exemplary numerical thresholds are those used for parameters for $δ_θ$, $φ_h$, Ψ and ℜ in the cascade rule based classification algorithm.

Referring again to FIG. 1, the system begins by loading the constant parameter generator 154 with predefined exemplary values (as shown in earlier parts of this disclosure for the parameters listed earlier) for $δ_θ$, $φ_h$, Ψ and ℜ. A human operator, viewer 168, commands the system to select the constant parameters through human intervention step 162 and parameter selection step 158. A feedback 164 from detection process 160 provides useful information to human intervention step 162 (e.g., by displaying of an intermediate result) for either staying on the current course or calling for a change of the operation. If the latter is true, the human operator can halt the operation through human intervention step 162 and adjust corresponding parameters $\delta_\theta$, $\phi_h$, $\Psi$ and $\mathfrak{R}$(this action is represented by the step of using controllable parameter generator 152). Then the human operator, viewer 168, commands the system to select the controllable parameters through human intervention step 152 and parameter selection step 158.

The system configuration/reconfiguration also includes the selection of different workflows that are shown in FIGS. 2A and 2B and FIGS. 3A and 3B.

Presented in the present invention are a method and a system of configurable microcalcification detection for mammography CAD. The system parameters are from a plurality of different parameter generating sources, at least one of which is controllable by human input.

Figure 14:
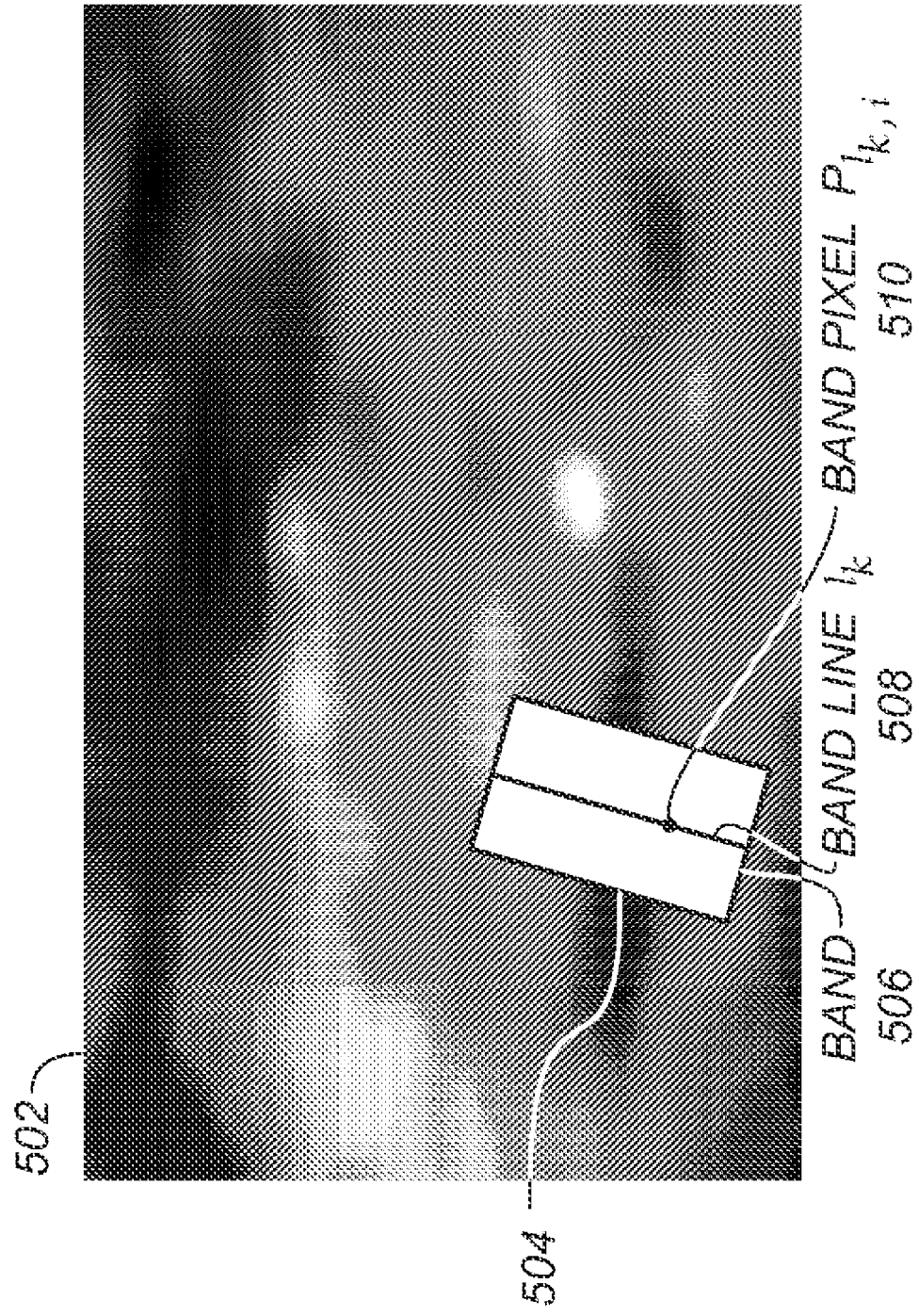
FIG. 14 is a graph illustrating a design to compute an eigenvalue band integral profile for an object in a digitized mammogram according to an embodiment of the present invention.

It should be noted that, in general, algorithms such as the one in the present invention do not distinguish concave and convex objects in images. Also, it can be noted that the linear structures to be verified in mammograms (images) typically appear to be brighter than other background contents. An exemplary ROI 502 is shown in FIG. 14 with an object 504 that is not a type of line structure presently sought. To rule out this type of false line structure, constructed in the present invention is a method of classifying convexity and concavity of detected linear structures. A method for classifying convexity and concavity of verified linear structures is an eigenvalue band integral profiling in one embodiment of the present invention.

Figure 15A:
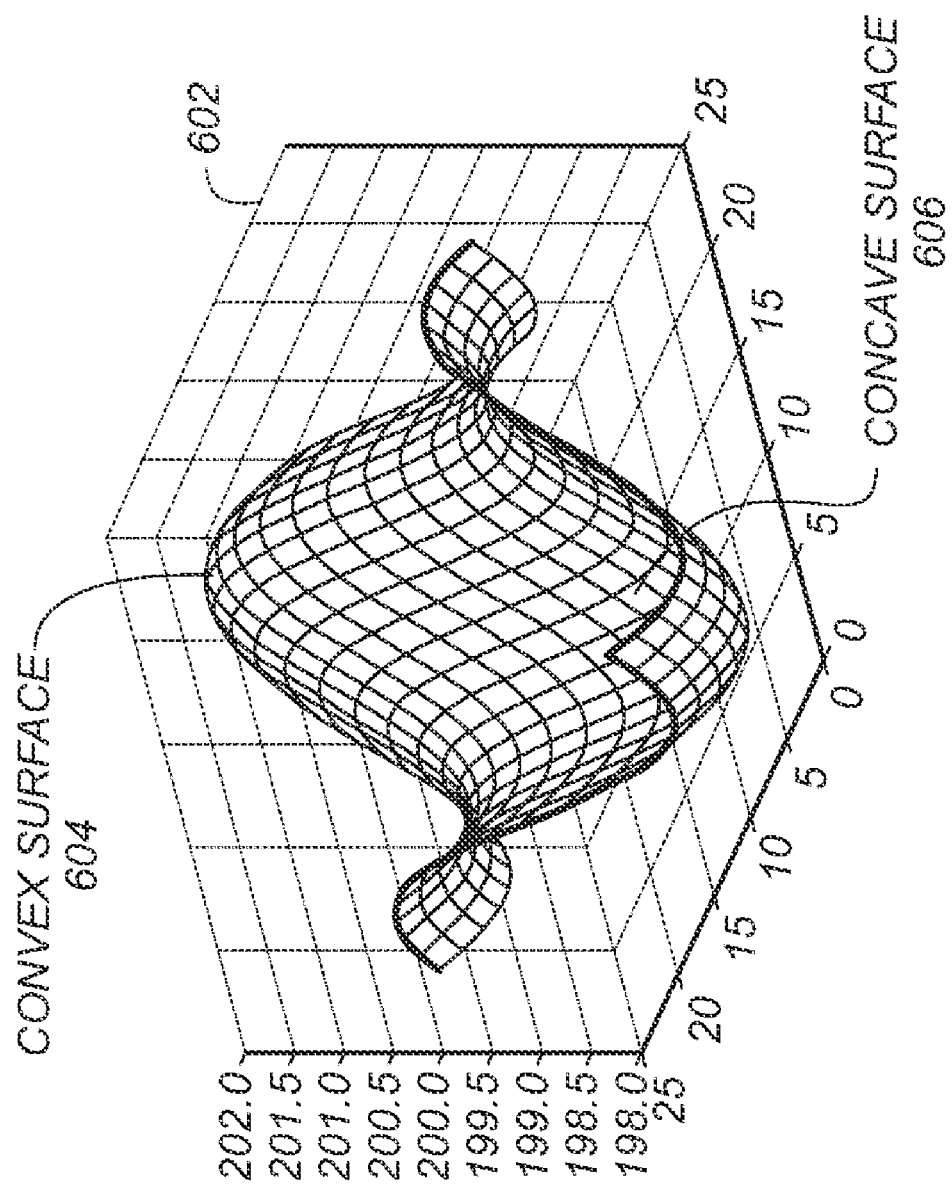
FIGS. 15A and 15B show, for an image that has a convex surface and a concave surface, respectively, an image of corresponding eigenvalues.
Figure 15B:
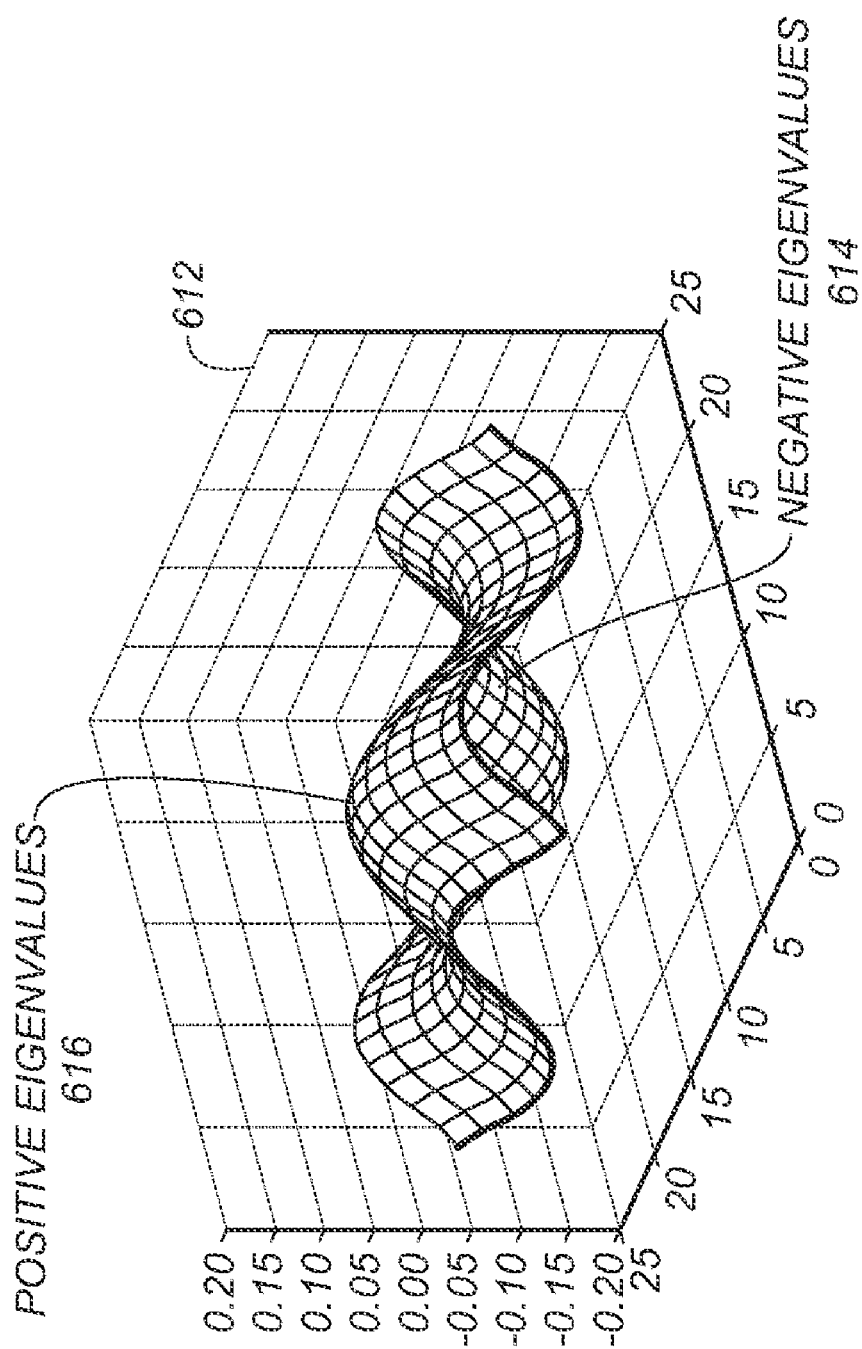

A graph 602 in FIG. 15A shows a convex surface 604 and a concave surface 606 illustrating intensity profiles for an arbitrarily image. A graph 612 in FIG. 15B shows the corresponding eigenvalue profiles of graph 602. Note that a convex surface 604 has negative eigenvalues 614 and a concave surface 606 has positive eigenvalues 616. The steps of computing eigenvalues of a surface are described subsequently.

Denote ROI 502 by image I. Define a band 506 that covers part of the object (surface) 504. Denote a band line 508 in a band 506 by $l_k$. Denote the position of a pixel 510 on line 508 within band 506 by $p_{l_k,i}$. Denote the code value (intensity) of pixel 510 by $I(p_{l_k,i})$. Construct a Hessian matrix $H=\{h_{m,n}\}$ for each of the pixels within the band 506 with the formula:

$$H(I(p_{l_k,i})) = \{h_{m,n}\};$$
$$h_{m,n} = \frac{\partial I}{\partial x_m \partial x_n}; m \in [1, 2]; n \in [1, 2].$$

Where $x_m$ and $x_n$ signify two orthogonal axes of image I, and element $h_{m,n}$ is a partial derivative. Solve the following matrix equation to obtain eigenvalues $\lambda_1$ and $\lambda_2$ for every pixel $p_{l_k,i}$ within band 506:

$$H = E\Lambda E^{-1};$$
$$E = [e_1, e_2];$$
$$\Lambda = \begin{bmatrix} \lambda_1 & 0 \\ 0 & \lambda_2 \end{bmatrix},$$

where $e_1$ and $e_2$ are 2 by 1 column vectors (eigen vectors). The sign of the eigenvalues indicates the surface orientation, either concave or convex. In the present invention, to evaluate the surface orientation, a metric, S, is defined as eigenvalue band integral profile to verify object surface property (convexity and concavity). The element of the eigenvalue band integral profile, S, is computed as $$s_i = \sum_{k=1}^{W} \tilde{I}(p_{l_k,i}) \text{ where } \tilde{I} = \{\lambda_1(p_{l_k,i}) + \lambda_2(p_{l_k,i})\}$$

and W is the number of lines within the band.

Figure 16:
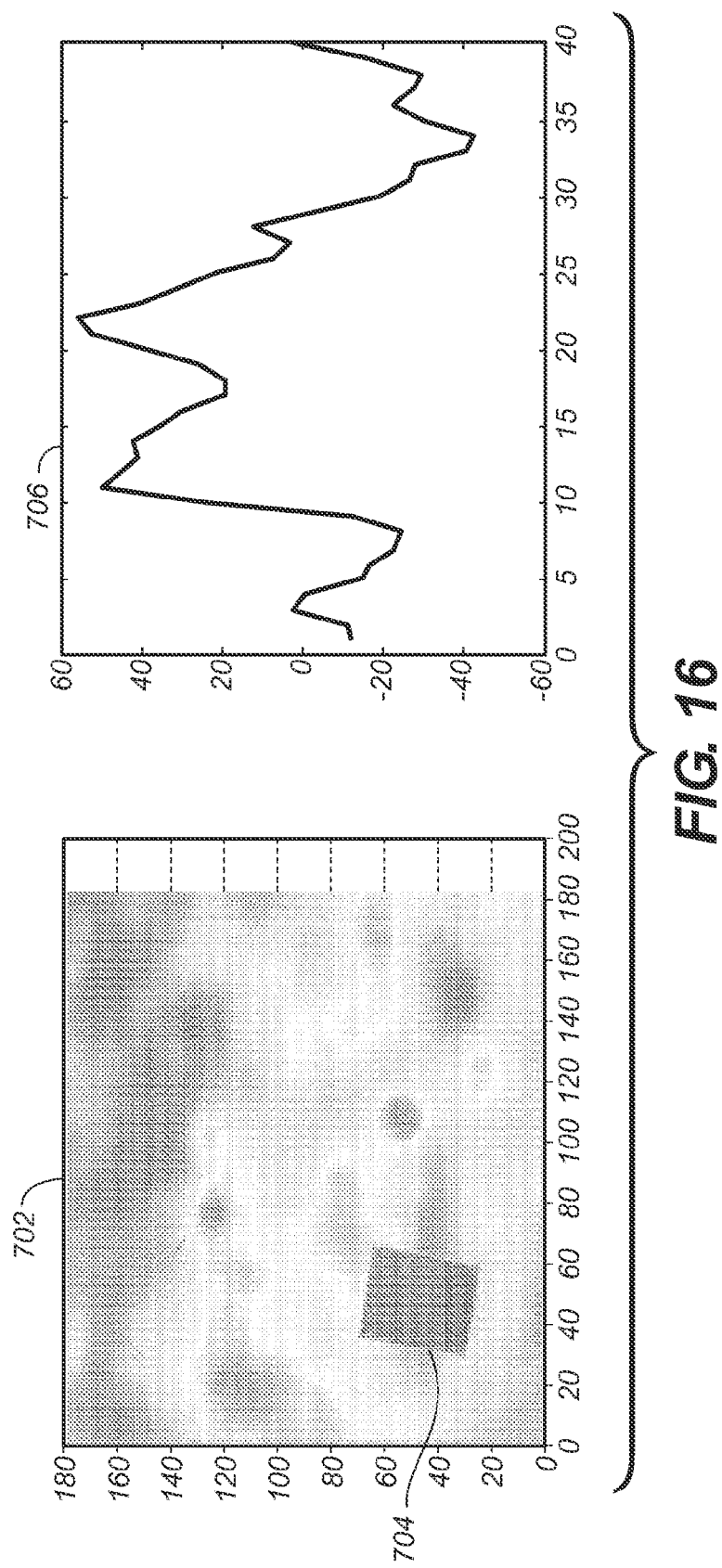
FIG. 16 is an illustration of an exemplary band that covers an object in a region of interest in a digitized mammogram and the corresponding actual eigenvalue band integral profile.

FIG. 16 shows a graph of an actual ROI 702 of a digitized mammogram. A band 704 covers part of an object in ROI 702. An eigenvalue band integral profile 706 on the right displays the actual eigenvalue band integral profile for the pixels within band 704. The positive curve of the eigenvalue band integral profile indicates that the object covered by band 704 in ROI 702 has concave type surface in terms of its intensity values.

Those skilled in the art can appreciate that metrics other than eigenvalue band integral profile, as used in the present invention, such as intensity profiles for example, could be employed for the purpose of classifying image object surface convexity and concavity.

Using Cognitive Functions Principles

Although the pattern recognition algorithms described earlier provide a powerful set of utilities for automatically detecting microcalcifications and other cancerous lesions, their results are subject to review by a practiced diagnostician. As is well-known to those skilled in the art of automated image analysis techniques, pattern recognition algorithms can detect cancerous lesions (microcalcifications in the above examples) in mammographic test images but, by nature, also capture false-positive lesions as well. Therefore, any set of cancerous lesions that is reported by such algorithms typically includes both true positives (TPs) and false positives (FPs). Embodiments of the present invention are directed to the problem of how the results of diagnostic pattern recognition routines can be more effectively presented to the diagnostician. Display techniques used in embodiments of the present invention help to highlight detection results for the diagnostician and help to direct and hold the attention of the diagnostician so that detected MCCs in the breast image can be more effectively examined and diagnosed.

To aid in diagnosis, the display techniques used in embodiments of the present invention adapt and employ one or more principles of cognitive functions. These principles, well-known to those skilled in behavioral and perceptual psychology and psychophysics, take advantage of empirical results and inferences drawn from experimental data on how people process, learn, and retain visual data. Among some of the principles utilized in various embodiments of the present invention for this purpose are the following:

(i) Synchronization. One principle of cognitive functions relates to synchronization. The principle of synchronization states that parts of the neural system that participate in some cognitive task transiently synchronise their activities. For example, in feature binding, neuronal ensembles representing different features (e.g., colour, shape, etc.) may synchronise their activities in order to signal that the features belong to the same object. There is confirmation, both from experimental and modeling approaches, that this principle is extremely powerful and many cognitive functions, such as selective attention, for example, can be considered from this point of view.

(ii) Attention and adaptation. Franco Pestilli et al. discuss visual attention and adaptation in a recently published article "How do attention and adaptation affect contrast sensitivity?", *Journal of Vision*, 7(7):9, 1-12 currently at the internet address accessible from journalofvision.org/7/7/9, 2007. As noted in the Pestilli et al. article, visual attention is a key mechanism that enables the brain to optimize performance within given metabolic limits. Attention can be allocated covertly, without eye movements. Covert attention allows us to prioritize the processing of some locations of the visual scene at the expense of others via a "push-pull" mechanism. Both temporal and spatial aspects of visual information processing are enhanced by directing attention to a location in the visual field. Such enhancements at the attended location happen early in the visual stream and are accompanied by concurrent impairment at unattended locations. The pervasiveness of this push-pull mechanism is evidenced by the finding that contrast sensitivity is increased at attended locations but is decreased at unattended locations, even with very sparse displays. Psychophysical studies reveal two subsystems of covert attention. Sustained or endogenous attention is voluntary and allocates perceptual resources according to task demands. By contrast, exogenous or transient attention is involuntary and allocates resources to the location where a sudden change in stimulation occurs, for example, a change in luminance, contrast, or color. These two subsystems are mediated by partially segregated networks of brain areas. The neural response to contrast is, at least in the first stages of the visual system, monotonic across the full contrast range. With attention, less contrast is necessary to attain the same response level, and stimulus contrast appears to be more intense.

(iii) Contrast. The visibility of every image can be directly related to its contrast, which delineates what is visible to us and is the basis of subsequent analyses performed on the visual input. Therefore, maintaining the best sensitivity to contrast in the environment is a primary task for the visual system. The sensitivity of individual neurons is restricted to a short contrast range, with neurons responding weakly at low contrast levels; their response increases monotonically across a limited range of contrast values before saturating. Contrast adaptation enables us to act in environments containing extremely wide contrast ranges, despite the fact that neurons have a limited dynamic range with respect to contrast. This reduces the visual system's response to static, unchanging stimuli, while optimizing sensitivity to the most informative scene-characteristic differences around the time-averaged contrast level. Looking at a stimulus for an extended time reduces our sensitivity to that stimulus and to similar stimuli as a result of a decreased neuronal response.

Figure 17:
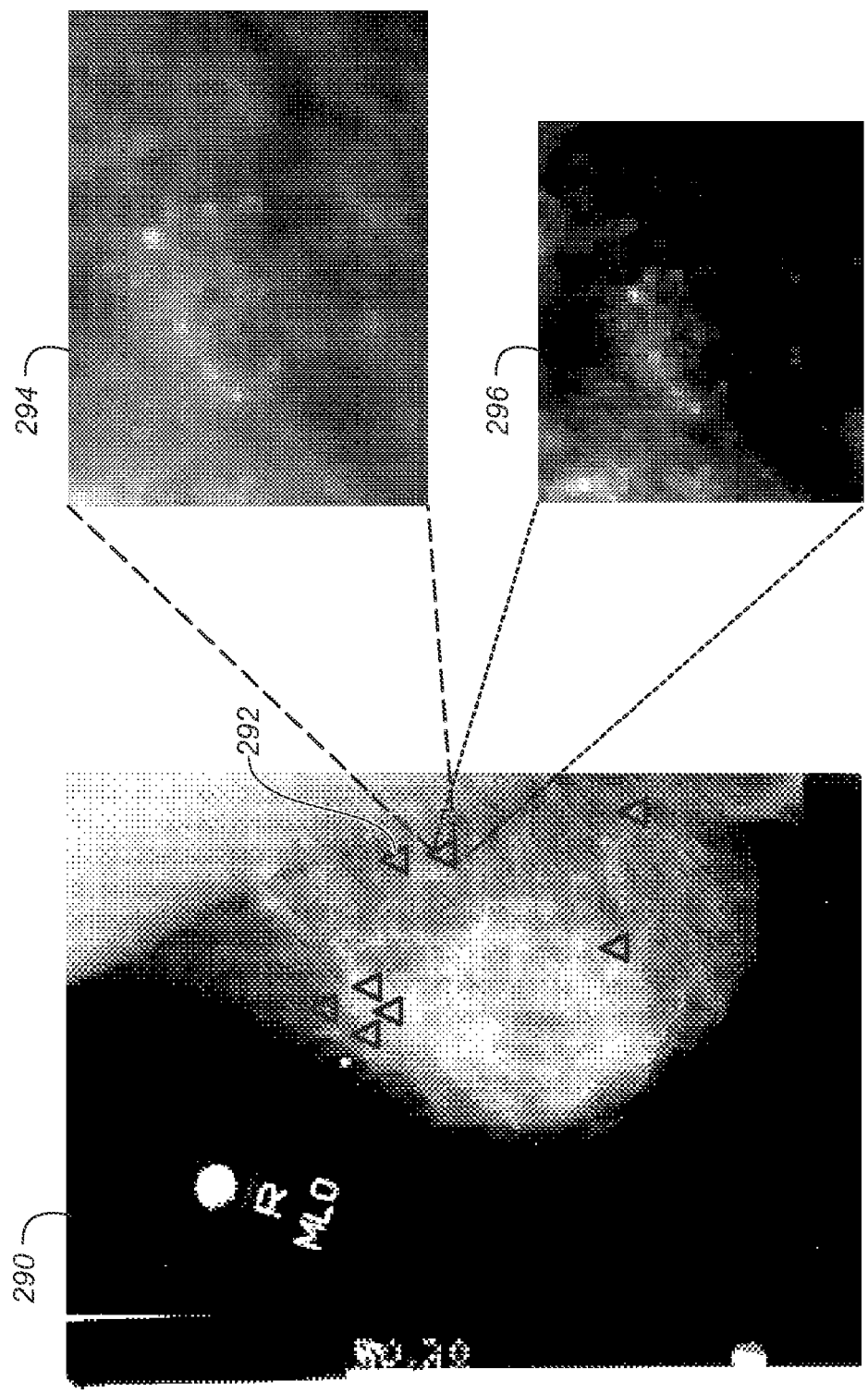
FIG. 17 illustrates a mammographic image with marks at locations of detected lesions and showing, for one of the locations, presentation of image content under different contrast display settings.

Now referring to FIG. 17, there is shown a mammographic test image 290. The mammographic image, or at least a relevant portion of this image, is displayed with triangle marks (e.g. a mark 292) at the locations of system-detected cancerous lesions (candidate MCC set). Note that these automatically detected cancerous lesions can contain both true positives and false positives. Each detected lesion is then verified by the diagnostician. An embodiment of the present invention assists the diagnostician by a sequence, shown in the logic flow diagram of FIG. 18, that does the following:

(1) Obtain the diagnostic image in an image acquisition step 370.

(2) In a feature detection step 372, detect at least one feature, such as an MCC cluster for example, in the acquired image by applying one or more pattern recognition algorithms, such as those described earlier. This step takes advantage of the range of existing pattern recognition algorithms that have been developed for MCC detection over the last several years as well as allowing for the ongoing development and implementation of newer pattern recognition techniques.

(3) Display the image in a display step 374, adding a marking on the display for each feature detected in step (2).

(4) Accept selection, by the diagnostician, of a candidate feature from the set. This is performed using a viewer instruction step 378, as described in more detail subsequently.

(5) To begin a display step 380, display the selected candidate MCC cluster or other feature, generally without the marking, under a first set of display settings 388 for a first interval of time. The first set of display settings can include any of a number of display characteristics, including contrast, luminance, color, spatial-position shifting, or filtering, for example. The displayed image may be shown with pixels in the conventional intensity imaging domain or, alternately, with pixels in a different imaging domain, such as in a gradient magnitude domain, for example.

(6) Display the selected candidate MCC cluster or other feature under at least a second set of display settings for a second interval of time. The second set of display settings may change any suitable image value that enhances feature visibility by taking advantage of principles of cognitive functions. Among settings that can be changed are relative contrast, luminance, filtering, color, pixel spatial position, or imaging domain type, for example. The selected MCC cluster or other feature can then optionally be displayed under third and additional settings as desired, for example.

(7) Optionally, repeat steps (5) and (6) one or more times for the candidate MCC.

Viewer instruction step 378 allows the viewing radiologist or other diagnostician to specify the sequence of display of candidate MCC clusters or other features. Using viewer instruction step 378, the displayed features themselves can be selected for close-up viewing as candidate MCCs or clusters either manually, one at a time, or automatically, such as using a progressive self-timed sequence. Upon being manually selected, the image contents at each selected location are displayed first as a separate image 294, as is shown in FIG. 17. In the embodiment shown, image 294 includes the detected lesion and its surroundings. Note that image 294 may display at a higher resolution than does the full displayed image 290. The image contents of image 294 are subject to the operations of steps (5) (6) and (7) as previously described and may be represented on the display by image pixel intensity values or image pixel intensity derivative values such as intensity gradient magnitude values.

Viewer instruction step 378 can use any of a number of different types of user interaction for obtaining the instruction. With the image displayed in display step 374 of step (3), for example, the viewer may enter an instruction specifying one or another feature in any of a number of ways. The viewer can use a pointer, such as a mouse, joystick, or other cursor manipulating device or a touchscreen entry. Optionally, a typed command specifying a feature for viewing can be entered. In another embodiment, an audible verbal command can be obtained as a viewer instruction, enabling the radiologist to work in a hands-free manner. In yet another hands-free embodiment, eye gaze tracking is used as a method of entering an instruction, to automatically sense the location of the viewer's attention and, in response, to display the corresponding feature under selected display settings. Various hands-free modes of instruction entry are well known to those skilled in the user interface arts.

Figure 18:
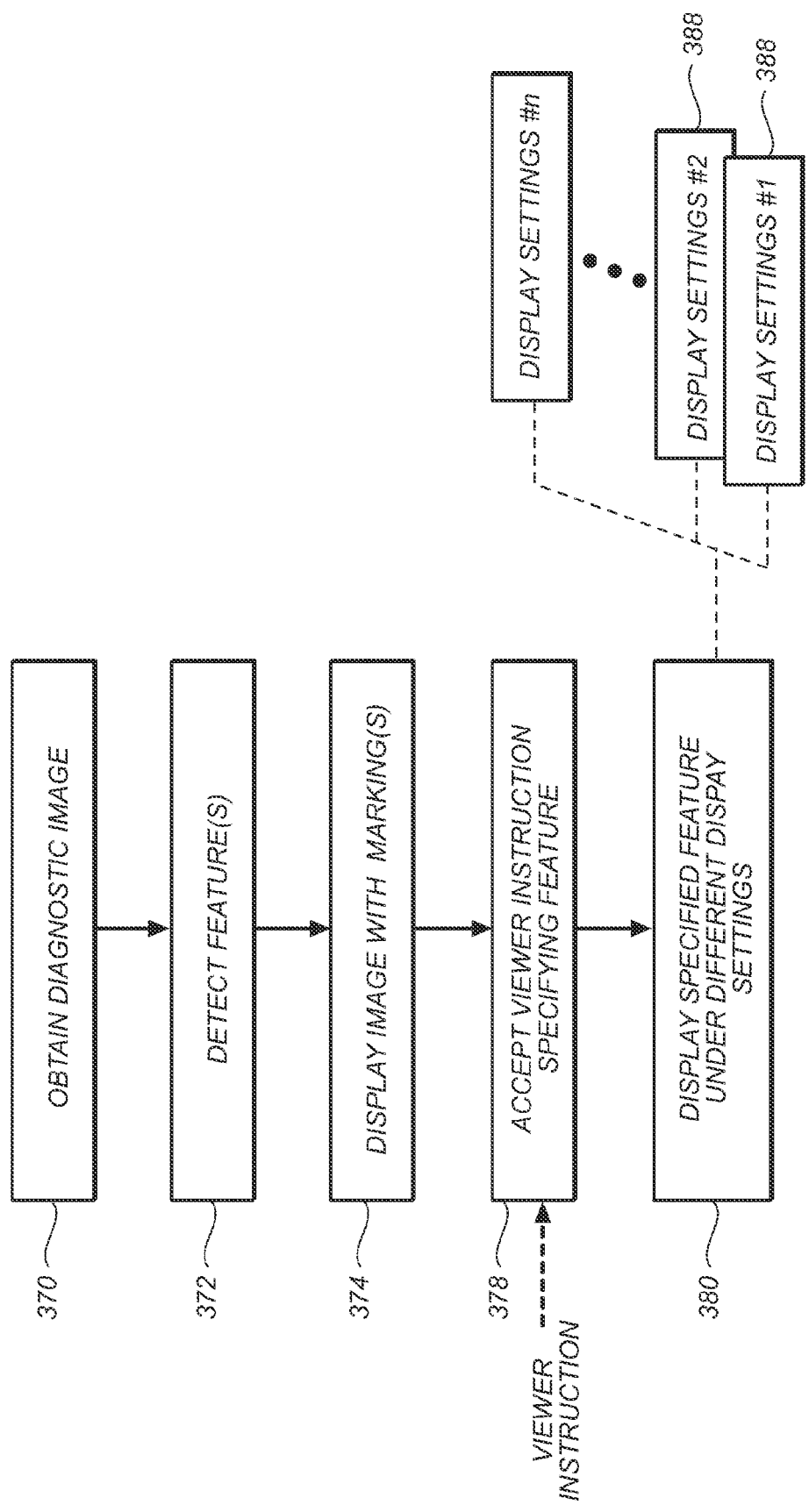
FIG. 18 is a logic flow diagram showing operational steps for assisting the diagnostician by suitable display of image features, according to one embodiment of the present invention.

As part of the process of FIG. 18, user interaction can also be used to allow viewer selection of image display settings 388. For example, a particular diagnostician may prefer alternating changes in color or luminance over changes in image contrast for viewing specific types of lesions. Thus, for example, a particular viewer can set up a preferred set of display settings for personal use when viewing diagnostic images. In one embodiment, the viewer has the option to change the first and second display settings dynamically, as the image is being viewed, for example.

The selected location may also be displayed in place in the original image. In such a case, the selected location appears as a window, with a portion of the image magnified and displayed on top of or within the on-screen boundaries of original image 290. The contents within the window are subject to the operations of steps (5) (6) and (7) described previously.

As part of the display in step (5), the first image 294, as shown in the embodiment of FIG. 17, is displayed in a certain contrast setting that is controlled by a display mechanism for a given duration, as one representation form. An exemplary duration for display as image 294 could be 0.5 seconds. At the end of the display duration of image 294, the image contents of the candidate MCC at the selected location are displayed as a second separate image 296. The second image 296, as shown in FIG. 17, is displayed using a different contrast setting that is controlled by the display mechanism as another representation form. The display duration of image 296 may also be regulated by the display mechanism. An exemplary duration could be 0.6 seconds.

In one embodiment, the separate images such as 294 and 296 are displayed at a suitable location on the display screen that lies outside the original image 290. That is, the same area or window of the display screen first shows image 294, then shows image 296 displayed in place of image 294.

This display process of steps (5)-(7) above can repeat for the same MCC candidate as the detected feature and can then continue for a total of N separate images, with N different representation forms for displaying the image contents at the selected location. An exemplary value for N could be 10. This display process for N separate images can be repeated automatically with the same N different contrast or other display settings for M times. An exemplary value for M could be 10. The process can be manipulated by the viewer, such as to speed up, slow down, or pause the display when showing an image under specified settings, for example. The viewer may enter a command to extend a particular display interval.

The automatic display mechanism can be overridden by command entry from the viewer using any of a number of command entry devices or techniques, as noted earlier. Other variables, such as the selected set of display settings, can also be changed by viewer instructions as the image is displayed.

With the use of such a varying display process, an image feature such as a microcalcification or an image background object may have a more pronounced appearance under a first set of display conditions, as a first representation form, than under a second set of display conditions, as a second representation form. With this arrangement, the same image feature may appear, then effectively "disappear" synchronously, attracting the viewer's attention thereby. This technique uses the synchronization mechanism noted in (i) above to stimulate the contrast sensitivity of the viewer's visual system. Thus, using this synchronous sequencing, the viewing diagnostician is able to more effectively verify whether a feature in a mammography image is a false- or true-positive feature.

Figure 19:
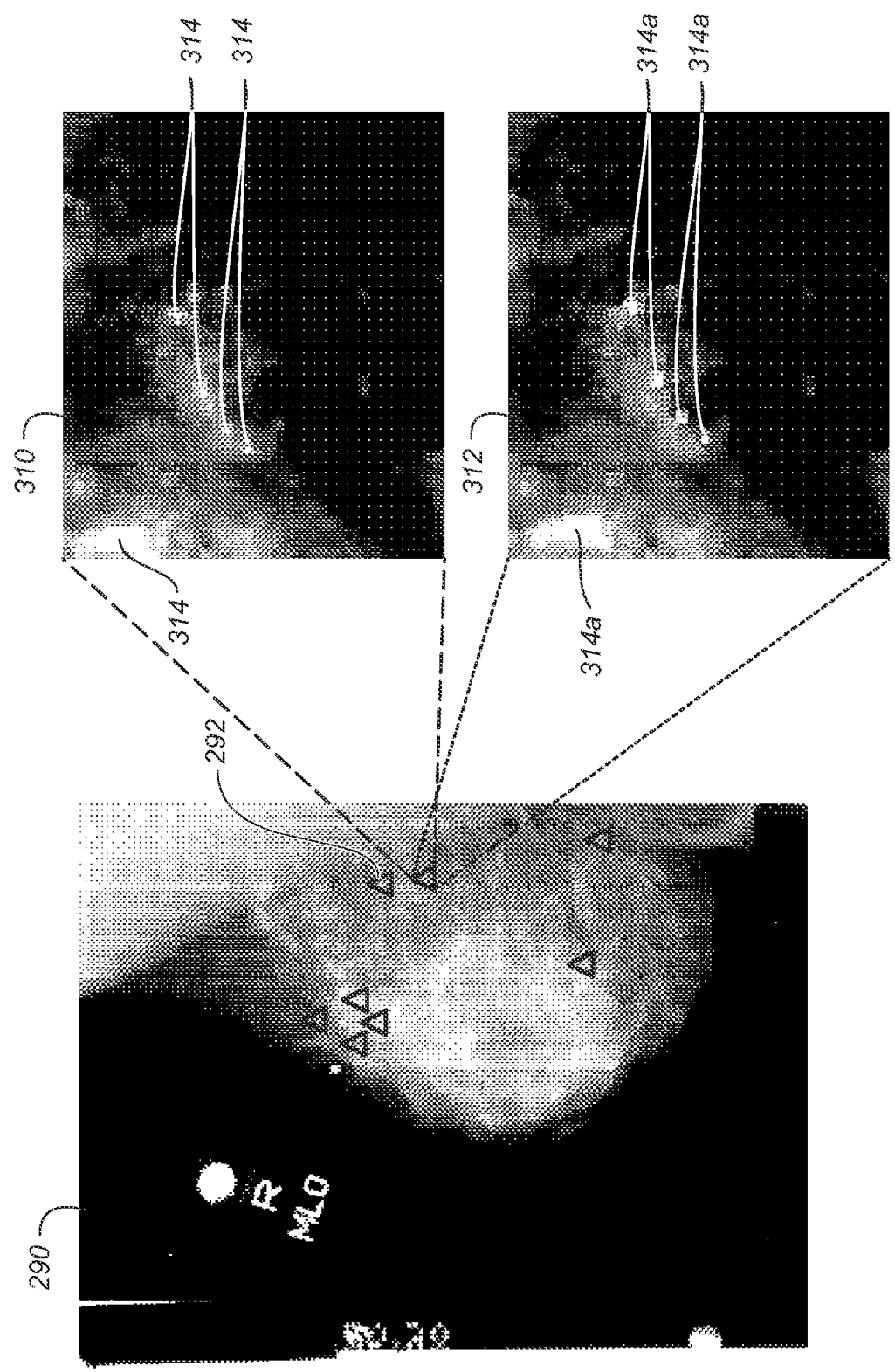
FIG. 19 shows a mammographic image with marks at locations of detected lesions and showing, for one of the locations, presentation of image content with spatial shift applied to suspected microcalcifications.

FIG. 19 shows display of mammographic image 290 in an alternate embodiment that uses different display settings. Again, marks indicate locations of detected lesions. An enlarged image 310 shows one view with suspected microcalcifications 314. A second enlarged image 312 shows the same area under a different set of display conditions, with shifted microcalcifications 314*a*, their pixels spatially shifted in this view in order to highlight their presence to the viewing radiologist. By shifting pixel positions for these features slightly between two image representations, this method uses visual tools based on cognitive perception functions to attract the attention of the diagnostician to detected MCC features. Changes in color representation or in image filtering can alternately be used and images having different treatment shown synchronously in similar manner to accentuate image features. Shifting pixel positions for particular features between consecutive image representations also helps to highlight, for the diagnostician, what has been detected by recognition algorithms that operate at the pixel cluster level. This can help direct the attention of the diagnostician to the underlying tissues that are represented by the pixel clusters.

Figure 8:
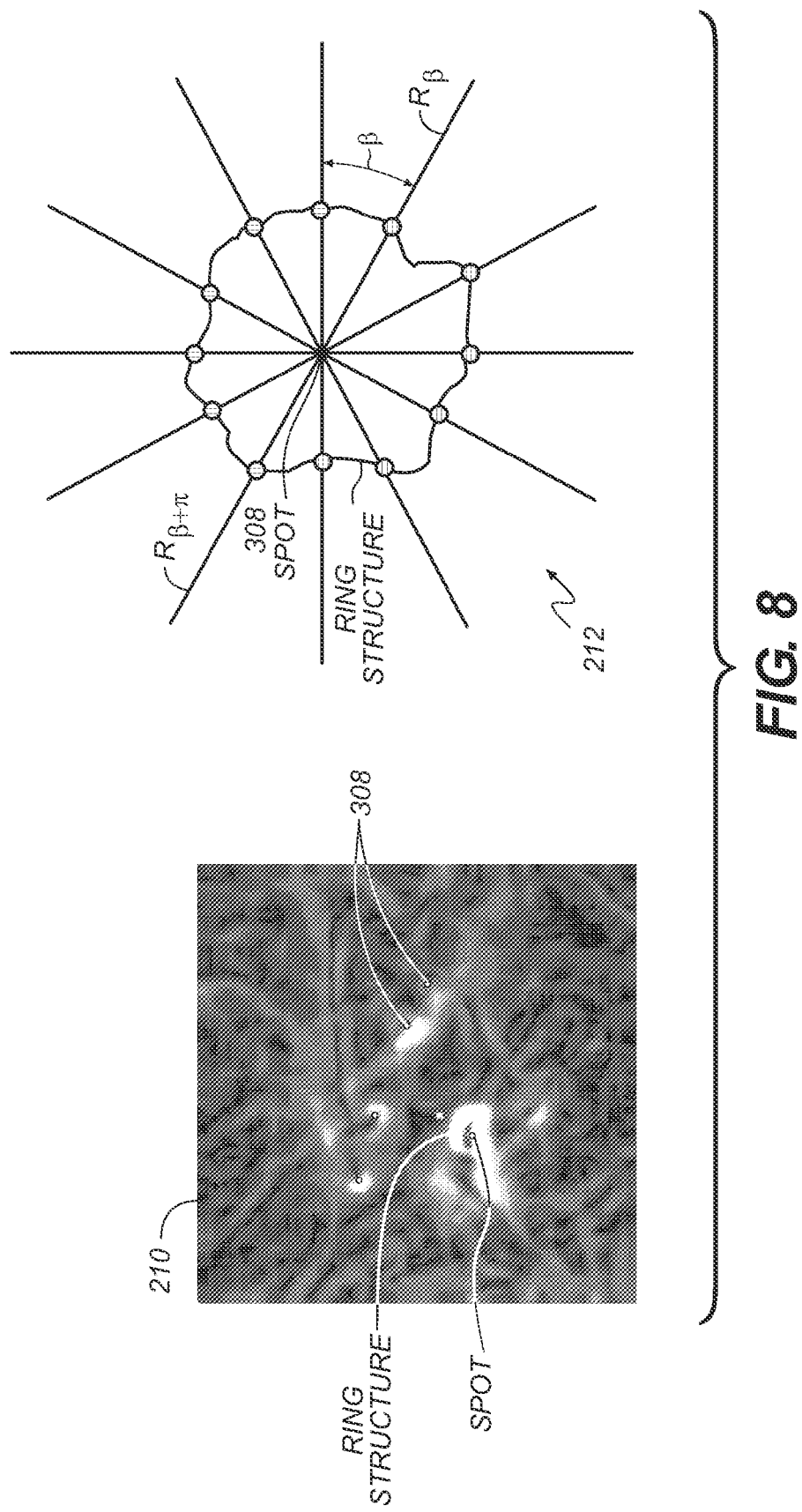
FIG. 8 displays an exemplary region of interest with ring-like structure and a graph illustrating a ring-like structure search method.

As discussed earlier under Additional Measure for TP Protection, true MCC clusters may have topological ring-like structures nearby, more readily observable and detectable in intensity gradient magnitude space than in intensity space (for example, see gROI 210 in FIG. 8). These structures often define areas within which there are one or more microcalcification spots and other features that can be highlighted for more effective display using shifting pixel positions, as described in the preceding paragraph. Using principles of cognitive functions, as described herein, MCC spots within such areas can be made more readily visible to the viewing diagnostician.

Marks for indicating MCC candidates may use any of a number of possible colors and shapes and may differ from the triangles shown in example displays given herein. The pattern recognition algorithms described earlier can capably assign a ranking to one or more MCC candidates. MCC candidates with lower rank, and thus more likely to be FPs, may be marked with triangles of a color different from those with higher ranks. In practice, it may be valuable to display the more questionable MCC candidates using different visual handling than with other MCC candidates in order to allow closer scrutiny where computer results may not be as accurate.

This type of display mechanism contains computer hardware and an image display device, and is controlled by display software that utilizes display algorithms that are built on principles of cognitive functions, such as those just described. It will be understood that the computer program product of the present invention may make use of a number of image manipulation algorithms and processes that are well known.

The present invention is described as a method. However, in another embodiment, the present invention comprises a computer program product for abnormality detection for medical diagnostics and decision support in accordance with the method described. In describing the present invention, it should be apparent that the computer program of the present invention can be executed by any well-known type of computer system, such as using a workstation or personal computer. However, many other types of computer systems can be used to execute the computer program of the present invention. Thus, it will be understood that a computer program product embodiment of the present invention may embody algorithms and processes not specifically shown or described herein that are useful for implementation. Such algorithms and processes are within ordinary skill in the display arts.

Additional aspects of such algorithms and systems, and hardware and/or software for producing and otherwise processing the images or co-operating with the computer program product of the present invention, are not specifically shown or described herein and may be selected from algorithms, systems, hardware, components and elements known in the art.

A computer program for performing the method of the present invention may be stored in a computer readable storage medium. This medium may comprise, for example; magnetic storage media such as a magnetic disk (such as a hard drive or a removable disk) or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer-readable storage medium that is connected to the image processor by way of the internet, other network type, or other communication medium. Those skilled in the art will readily recognize that the equivalent of such a computer program product may also be constructed in hardware.

It will be appreciated that variations and modifications can be effected by a person of ordinary skill in the art without departing from the scope of the invention. For example, any of a number of methods can be used for setting up sets of image display settings or for editing existing sets of display settings. The subject matter of the present invention relates to digital image processing and computer vision technologies, which is understood to mean technologies that digitally process a digital image to recognize and thereby assign useful meaning to human understandable objects, attributes or conditions, and then to utilize the results obtained in the further processing of the digital image. Although the particular examples described herein have been primarily directed to mammography applications, it can be appreciated that the scope of the present invention also extends to diagnostic imaging applications of other types.

The invention has been described in detail with particular reference to presently preferred embodiments, but it will be understood that variations and modifications can be effected within the scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LISTS

| PARTS LIST | |
|---|---|
| 150 | detection system |
| 152 | controllable parameter generator |
| 154 | parameter generator |
| 156 | mammographic test images |
| 158 | parameter selection step |
| 160 | detection process |
| 162 | human intervention step |
| 164 | feedback |
| 168 | viewer |
| 174 | command line |
| 176 | path |
| 180 | MCC detector training system |
| 182 | cancerous mammographic images |
| 184 | normal mammographic images |
| 202 | sketch of a linear structure and a band |
| 204 | sketch of a linear structure and a band |
| 208 | linear structure |
| 210 | region of interest |
| 212 | graph |
| 222 | region of interest |
| 230 | graph |
| 232 | graph |
| 238 | graph |

| PARTS LIST -continued | |
|---|---|
| 240 | graph |
| 242 | graph |
| 244 | graph |
| 246 | graph |
| 254 | pre-processing step |
| 256 | feature extraction step |
| 257 | reduction step |
| 258 | cluster feature extraction step |
| 260 | MCC detection step |
| 280 | graph |
| 290 | image |
| 292 | mark |
| 294 | image |
| 296 | image |
| 302 | region of interest |
| 304 | region of interest |
| 308 | spot |
| 310 | enlarged image |
| 312 | shifted enlarged image |
| 314 | microcalcification |
| 314a | shifted microcalcification |
| 352 | algorithm step |
| 357 | algorithm step |
| 360 | feature selection and MCC detector training step |
| 370 | image acquisition step |
| 372 | feature detection step |
| 374 | display step |
| 378 | viewer instruction step |
| 380 | display step |
| 388 | display settings |
| 402 | mammogram |
| 404 | region of interest |
| 502 | graph (region of interest) |
| 504 | object |
| 506 | band |
| 508 | band line |
| 510 | pixel |
| 602 | graph |
| 604 | convex surface |
| 606 | concave surface |
| 612 | graph |
| 614 | negative eigenvalues |
| 616 | positive eigenvalues |
| 702 | region of interest |
| 704 | band |
| 706 | eigenvalue band integral profile |
| 801 | mammographic image |
| 802 | boundary |
| 804 | cluster |
| 806 | breast |
| 810 | mammographic image |
| 812 | boundary |
| 814 | cluster |
| 816 | breast |

What is claimed is:

1. A method for displaying a diagnostic digital image, comprising:

acquiring the diagnostic digital image;

applying one or more pattern recognition algorithms to the acquired diagnostic digital image and detecting at least one feature within the acquired diagnostic digital image;

displaying at least a portion of the acquired diagnostic digital image with a marking at the location of the at least one detected feature; and displaying, so as to stimulate a contrast sensitivity of a viewer's visual system:

(a) at least a portion of the acquired diagnostic image comprising the at least one detected feature under a first set of image display settings including a first contrast for a first specified time interval; and (b) automatically displaying the at least a portion of the acquired diagnostic image comprising the at least one detected feature under at least a second set of image display settings including a second contrast for a second specified time interval.

2. The method of claim 1 wherein the first set of image display settings further differ from the second set of image display settings with respect to at least one of: luminance, image filtering, image color, imaging domain, and pixel spatial position.

3. The method of claim 1 further comprises repetitively alternating displaying between the first and second sets of image display settings.

4. The method of claim 1 comprising displaying the at least one detected feature within boundaries of the displayed at least portion of the acquired diagnostic digital image.

5. The method of claim 1 further comprising assigning a ranking to the at least one detected feature according to predetermined diagnostic criteria and reporting the assigned ranking.

6. The method of claim 5 wherein the displayed marking corresponds to the assigned ranking.

7. The method of claim 1 wherein the diagnostic image is a mammographic image and wherein the at least one detected feature is a microcalcification cluster.

8. The method of claim 1 further comprising responding to a command to extend either the first or second interval.

9. The method of claim 1 further comprising displaying the at least one detected feature under a third set of image display settings for a third interval.

10. A method of diagnosis for a mammographic image, comprising:
   obtaining a true-positive set comprising two or more mammographic images wherein each image in the true-positive set comprises one or more true-positive microcalcification clusters and exhibits cancer according to a ground truth measure;
   training an automated detector utility to detect a candidate microcalcification cluster in a mammographic test image according to features identified from the positive microcalcification clusters in images from the true-positive set;
   displaying, so as to stimulate a contrast sensitivity of a viewer's visual system:
   (a) at least a portion of the mammographic test image that includes the candidate microcalcification cluster using a first set of image display settings including a first contrast for a first specified time interval; and
   (b) automatically displaying the at least a portion of the mammographic test image that includes the candidate microcalcification cluster using a second set of image display settings including a second contrast for a second specified time interval.

11. The method of claim 10 further comprising alternating the use of the first and second sets of image display settings two or more times for displaying the portion of the mammographic test image that includes the candidate microcalcification cluster.

12. The method of claim 10 wherein the first and second sets of display settings further differ according to one or more of: luminance, image filtering, image color, imaging domain, and pixel spatial position.

13. The method of claim 10 further comprising configuring the first or second set of image display settings according to operator instructions.

14. The method of claim 10 further comprising applying pattern recognition to the mammographic image and displaying results of pattern recognition accordingly by changing pixel spatial position for one or more pixels.

15. A method for displaying a diagnostic digital image, comprising:
   acquiring the diagnostic digital image;
   applying one or more pattern recognition algorithms to the acquired diagnostic digital image and detecting at least one feature within the acquired diagnostic digital image;
   displaying at least a portion of the acquired diagnostic digital image with the at least one detected feature;
   accepting an instruction from a viewer specifying at least a first image display setting and a second image display setting;
   accepting an instruction from a viewer that specifies the at least one detected feature; and
   displaying, so as to stimulate a contrast sensitivity of a viewer's visual system, the at least one detected feature using the first image display setting including a first contrast for a first specified time interval, then using the second image display setting including a second contrast for automatically displaying the at least one detected feature for a second specified time interval.

16. The method of claim 15 wherein accepting the instruction from the viewer specifying either of or both of the first image display setting and the at least one detected feature comprises responding to an audible instruction.

17. The method of claim 15 wherein accepting the instruction from the viewer specifying either of or both of the first image display setting and the at least one detected feature comprises using gaze tracking.

18. The method of claim 15 wherein acquiring the diagnostic image comprises obtaining an x-ray.

19. The method of claim 1 further comprising displaying the at least a portion of the acquired diagnostic image comprising the at least one detected feature under a third set of image display settings including a third contrast for the first or second specified time intervals.

* * * * *